(12) United States Patent
Konyuba et al.

(10) Patent No.: US 10,541,111 B2
(45) Date of Patent: Jan. 21, 2020

(54) DISTORTION MEASUREMENT METHOD FOR ELECTRON MICROSCOPE IMAGE, ELECTRON MICROSCOPE, DISTORTION MEASUREMENT SPECIMEN, AND METHOD OF MANUFACTURING DISTORTION MEASUREMENT SPECIMEN

(71) Applicant: JEOL Ltd., Tokyo (JP)

(72) Inventors: Yuji Konyuba, Tokyo (JP); Kazuya Omoto, Tokyo (JP); Hidetaka Sawada, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 15/989,459

(22) Filed: May 25, 2018

(65) Prior Publication Data

US 2018/0342370 A1    Nov. 29, 2018

(30) Foreign Application Priority Data

May 26, 2017    (JP) .................................. 2017-105056

(51) Int. Cl.
*H01J 37/28*    (2006.01)
*H01J 37/26*    (2006.01)
*G01N 1/32*    (2006.01)

(52) U.S. Cl.
CPC ................ *H01J 37/28* (2013.01); *G01N 1/32* (2013.01); *H01J 37/265* (2013.01); *H01J 2237/1536* (2013.01); *H01J 2237/2802* (2013.01)

(58) Field of Classification Search
USPC .......................... 250/306, 307, 309, 310, 311
See application file for complete search history.

(56) References Cited

U.S. PATENT DOCUMENTS

2011/0049344 A1    3/2011  Dobashi et al.
2017/0077339 A1*   3/2017  Ma ........................ H01L 31/0693
2018/0012349 A1*   1/2018  Sakai ...................... H01J 37/22

FOREIGN PATENT DOCUMENTS

JP    2008171756 A    7/2008
WO    2009123311 A1   10/2009
WO    2016117104 A1   7/2016

OTHER PUBLICATIONS

Extended European Search Report dated Nov. 6, 2018 in EP18174280.0.

* cited by examiner

*Primary Examiner* — Nicole M Ippolito
(74) *Attorney, Agent, or Firm* — The Webb Law Firm

(57)    ABSTRACT

A distortion measurement method for an electron microscope image includes: loading a distortion measurement specimen having structures arranged in a lattice to a specimen plane of an electron microscope or a plane conjugate to the specimen plane in order to obtain an electron microscope image of the distortion measurement specimen; and measuring a distortion from the obtained electron microscope image of the distortion measurement specimen.

14 Claims, 30 Drawing Sheets

| | REGION SPECIFICATION | IMAGE AFTER PICK-UP OF MAXIMUM INTENSITY |
|---|---|---|
| FIRST (PROXIMAL) CIRCLE<br>−199.214 ,77.578<br>199.275 ,−77.5979<br>83.3355 ,202.648<br>−83.3575 ,−202.693<br>AVERAGE RADIUS 213.818 | | |
| SECOND CIRCLE<br>−282.362 ,−124.928<br>282.371 ,124.932<br>−116.21 ,280.128<br>116.215 ,−280.137<br>AVERAGE RADIUS 308.769 | | |
| THIRD CIRCLE<br>−166.192 ,−404.801<br>166.192 ,404.801<br>−398.43 ,155.072<br>398.43 ,−155.072<br>AVERAGE RADIUS 437.588 | | |
| FOURTH CIRCLE<br>232.355 ,−559.889<br>−232.355 ,559.889<br>−564.386 ,−250.064<br>564.386 ,250.064<br>AVERAGE RADIUS 606.189 | | |

FIG. 15

DISTORTION MEASUREMENT METHOD FOR ELECTRON MICROSCOPE IMAGE, ELECTRON MICROSCOPE, DISTORTION MEASUREMENT SPECIMEN, AND METHOD OF MANUFACTURING DISTORTION MEASUREMENT SPECIMEN

CROSS-REFERENCE TO RELATED APPLICATION

This application claims priority to Japanese Patent Application No. 2017-105056 filed May 26, 2017, the disclosure of which is hereby incorporated in its entirety by reference.

BACKGROUND OF THE INVENTION

Field of the Invention

The present invention relates to a distortion measurement method for an electron microscope image, an electron microscope, a distortion measurement specimen, and a method of manufacturing a distortion measurement specimen.

Description of Related Art

In a transmission electron microscope (TEM), an electron transmitted through a specimen passes through various lenses, an energy filter, and the like and reaches an image plane. An optical defect present in this process causes an aberration or a distortion in an obtained transmission electron microscope image (TEM image).

For example, JP-A-2008-171756 discloses a distortion measurement method for a transmission electron microscope image in a transmission electron microscope.

In addition, in a scanning transmission electron microscope (STEM) or a scanning electron microscope (SEM), for example, when implementing two-dimensional scanning with an electron probe in an XY plane, a distortion is created in a scanning transmission electron microscope image (STEM image) or a scanning electron microscope image (SEM image) when scanning in an X direction and scanning in a Y direction are not perpendicular to each other. In this manner, with a scanning transmission electron microscope or a scanning electron microscope, a distortion is created in an image when scanning with an electron probe is not carried out in an appropriate manner.

When a distortion occurs in an electron microscope image such as a TEM image, a STEM image, and a SEM image, problems such as an inability to accurately measure a length on a specimen and an inability to assess an accurate shape of the specimen arise. Therefore, there are demands for a measurement method that enables a distortion of an electron microscope image to be measured more accurately.

SUMMARY OF THE INVENTION

The invention provides a distortion measurement method that enables a distortion of an electron microscope image to be accurately measured, an electron microscope capable of accurately measuring a distortion of an electron microscope image, a distortion measurement specimen that enables a distortion of an electron microscope image to be accurately measured, and a method of manufacturing the distortion measurement specimen.

According to a first aspect of the invention, there is provided a distortion measurement method for an electron microscope image, the method including:
loading a distortion measurement specimen having structures arranged in a lattice to a specimen plane of an electron microscope or a plane conjugate to the specimen plane to obtain an electron microscope image of the distortion measurement specimen; and
measuring a distortion from the obtained electron microscope image of the distortion measurement specimen.

According to a second aspect of the invention, there is provided an electron microscope capable of measuring a distortion of an electron microscope image, the electron microscope including:
an image acquiring section that acquires an electron microscope image of a distortion measurement specimen having structures arranged in a lattice; and
a distortion measuring section that measures a distortion from the electron microscope image of the distortion measurement specimen.

According to a third aspect of the invention, there is provided a distortion measurement specimen for measuring a distortion of an electron microscope image, the distortion measurement specimen including:
a substrate; and
a pattern-formed layer supported by the substrate and including structures arranged in a lattice.

According to a fourth aspect of the invention, there is provided a method of manufacturing a distortion measurement specimen for measuring a distortion of an electron microscope image, the method including:
preparing a substrate;
forming a first layer on a first surface of the substrate;
forming structures arranged in a lattice by patterning the first layer; and
etching a second surface on an opposite side to the first surface to remove the substrate.

According to a fifth aspect of the invention, there is provided a distortion measurement method for an electron microscope image, the method including:
measuring a distortion of an electron microscope image by using an electron microscope image of a distortion measurement specimen manufactured by the method of manufacturing a distortion measurement specimen described above.

BRIEF DESCRIPTION OF THE DRAWINGS

FIG. 15 is a diagram illustrating a method of extracting an ellipse from an auto-correlation function.

Figure 1:
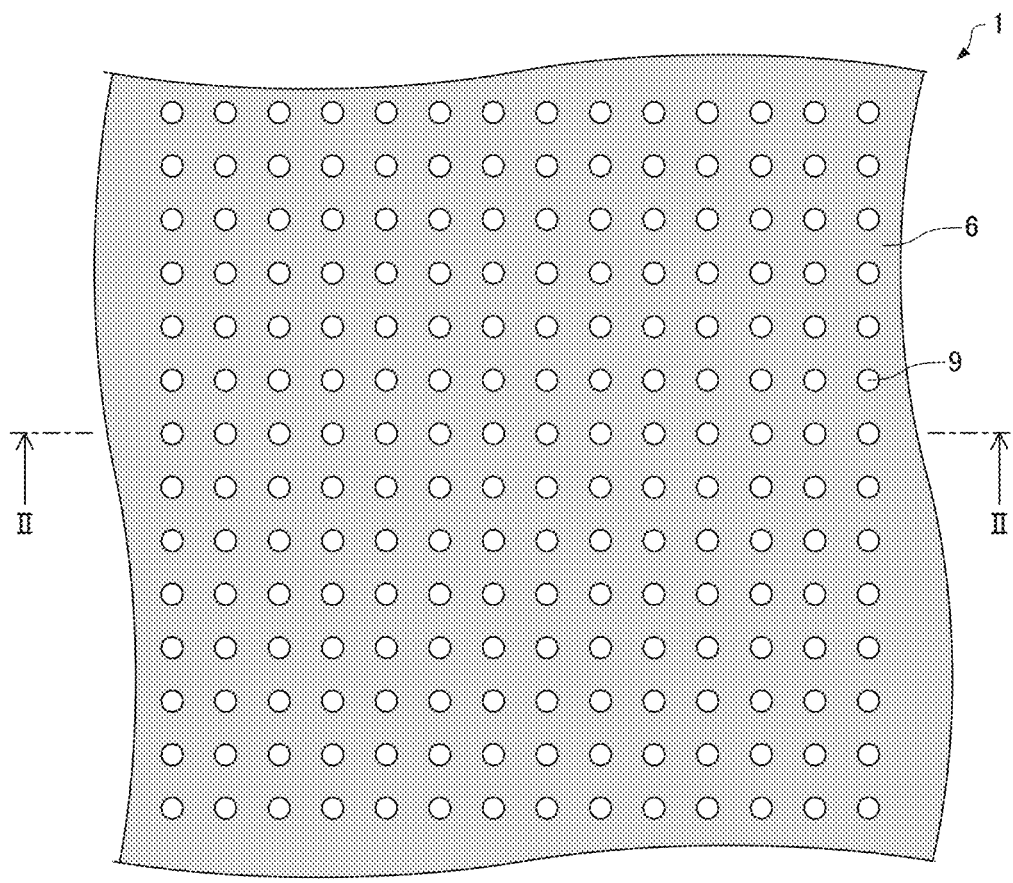
FIG. 1 is a plan view schematically illustrating a distortion measurement specimen according to an embodiment of the invention.

DESCRIPTION OF THE INVENTION (1) According to one embodiment of the invention, there is provided a distortion measurement method for an electron microscope image, the method including:

loading a distortion measurement specimen having structures arranged in a lattice to a specimen plane of an electron microscope or a plane conjugate to the specimen plane to obtain an electron microscope image of the distortion measurement specimen; and measuring a distortion from the obtained electron microscope image of the distortion measurement specimen.

With such a distortion measurement method for an electron microscope image, a distortion of an electron microscope image can be readily and accurately measured.

(2) In the distortion measurement method for an electron microscope image described above, the step of measuring a distortion may include:

calculating an auto-correlation function of the electron microscope image of the distortion measurement specimen; and measuring the distortion based on a pattern formed by connecting peak positions of the auto-correlation function.

With such a distortion measurement method for an electron microscope image, a distortion of an electron microscope image can be readily and accurately measured.

(3) In the distortion measurement method for an electron microscope image described above, the pattern may be an ellipse.

With such a distortion measurement method for an electron microscope image, a distortion of an electron microscope image can be readily and accurately measured.

(4) In the distortion measurement method for an electron microscope image described above, the pattern may be a concentric ellipse.

With such a distortion measurement method for an electron microscope image, a distortion of an electron microscope image can be measured more accurately.

(5) In the distortion measurement method for an electron microscope image described above, the step of measuring a distortion may include:

specifying positional coordinates of the structures on the electron microscope image of the distortion measurement specimen; and measuring the distortion based on a pattern formed by connecting the positional coordinates of the structures.

With such a distortion measurement method for an electron microscope image, a distortion of an electron microscope image can be readily and accurately measured.

(6) In the distortion measurement method for an electron microscope image described above, in the step of measuring a distortion, a grid pattern may be fitted to the pattern to calculate the distortion.

With such a distortion measurement method for an electron microscope image, a high-order distortion such as a barrel distortion and a pin-cushion distortion can be measured.

(7) In the distortion measurement method for an electron microscope image described above, the distortion measurement specimen may include:

a substrate; and a pattern-formed layer supported by the substrate and including the structures, and the structures may be through-holes, projected portions, or recessed portions.

(8) According to one embodiment of the invention, there is provided an electron microscope capable of measuring a distortion of an electron microscope image, the electron microscope including:

an image acquiring section that acquires an electron microscope image of a distortion measurement specimen having structures arranged in a lattice; and a distortion measuring section that measures a distortion from the electron microscope image of the distortion measurement specimen.

With such an electron microscope, a distortion of an electron microscope image can be readily and accurately measured.

(9) The electron microscope described above may further include:

an auto-correlation function calculating section that calculates an auto-correlation function of the electron microscope image of the distortion measurement specimen, and the distortion measuring section may measure the distortion based on a pattern formed by connecting peak positions of the auto-correlation function.

With such an electron microscope, a distortion of an electron microscope image can be readily and accurately measured.

(10) The electron microscope described above may further include:

a positional coordinate specifying section that specifies positional coordinates of the structures on the electron microscope image of the distortion measurement specimen, and the distortion measuring section may measure the distortion based on a pattern formed by connecting the positional coordinates of the structures.

With such an electron microscope, a distortion of an electron microscope image can be readily and accurately measured.

(11) The electron microscope described above may further include:

a display control section that performs control to cause a measurement result of the distortion as measured by the distortion measuring section to be displayed on a display section.

With such an electron microscope, a user can be readily informed of a measurement result of a distortion of an electron microscope image.

(12) The electron microscope described above may further include:

a distortion correcting section that corrects a distortion of a photographed electron microscope image, based on a measurement result of the distortion as measured by the distortion measuring section.

With such an electron microscope, an electron microscope image with no distortion (or reduced distortion) can be provided.

(13) The electron microscope described above may further include:

a scanning signal generating section that generates a scanning signal based on a measurement result of the distortion as measured by the distortion measuring section; and a scanning deflector that scans over a specimen with an electron beam in response to the scanning signal.

With such an electron microscope, an electron microscope image with no distortion (or reduced distortion) can be acquired.

(14) According to one embodiment of the invention, there is provided a distortion measurement specimen for measuring a distortion of an electron microscope image, the distortion measurement specimen including:

a substrate; and a pattern-formed layer supported by the substrate and including structures arranged in a lattice.

With such a distortion measurement specimen, a distortion of an electron microscope image can be readily and accurately measured.

(15) According to one embodiment of the invention, there is provided a method of manufacturing a distortion measurement specimen for measuring a distortion of an electron microscope image, the method including:

preparing a substrate;

forming a first layer on a first surface of the substrate;

forming structures arranged in a lattice by patterning the first layer; and etching a second surface on an opposite side to the first surface of the substrate to remove the substrate.

With such a method of manufacturing a distortion measurement specimen, since a semiconductor manufacturing technique can be used, a pattern made up of structures arranged in a lattice with high accuracy is formed on the first layer. Therefore, a distortion measurement specimen which enables a measurement of a distortion of an electron microscope image to be performed with high accuracy can be manufactured.

(16) The method of manufacturing a distortion measurement specimen described above may further include:

forming a second layer on the first layer, and the second layer may be a layer with conductivity.

With such a method of manufacturing a distortion measurement specimen, charging of the first layer can be prevented.

(17) In the method of manufacturing a distortion measurement specimen described above, in the step of forming structures, a resist for patterning the first layer may be exposed by an electron-beam lithography system.

With such a method of manufacturing a distortion measurement specimen, structures arranged in a lattice with high accuracy (for example, accuracy in the order of nm) can be formed on the first layer. Therefore, a distortion measurement specimen which enables a measurement of a distortion of an electron microscope image to be performed with high accuracy can be manufactured.

(18) In the method of manufacturing a distortion measurement specimen described above, in the step of forming structures, etching of the first layer may be performed by using an inductively-coupled plasma etching device.

With such a method of manufacturing a distortion measurement specimen, structures arranged in a lattice with high accuracy (for example, accuracy in the order of nm) can be formed on the first layer. Therefore, a distortion measurement specimen which enables a measurement of a distortion of an electron microscope image to be performed with high accuracy can be manufactured.

(19) In the method of manufacturing a distortion measurement specimen described above, in the step of forming the first layer, the first layer may be formed so that the first layer is imparted with tensile stress.

With such a method of manufacturing a distortion measurement specimen, wrinkles can be prevented from being created on the first layer even when the substrate is removed.

(20) In the method of manufacturing a distortion measurement specimen described above, the structures may be through-holes, projected portions, or recessed portions, and a shape of the structures as viewed from a thickness direction of the first layer may be a circle.

With such a method of manufacturing a distortion measurement specimen, through-holes can be formed with accuracy.

(21) According to one embodiment of the invention, there is provided a distortion measurement method for an electron microscope image, the method including:

measuring a distortion of an electron microscope image by using an electron microscope image of a distortion measurement specimen manufactured by the method of manufacturing a distortion measurement specimen described above.

With such a distortion measurement method for an electron microscope image, a distortion can be measured using an electron microscope image of a distortion measurement specimen in which a pattern constituted by structures arranged in a lattice is formed with high accuracy. Therefore, a distortion of an electron microscope image can be readily and accurately measured.

Embodiments of the invention are described in detail below with reference to the drawings. Note that the following embodiments do not unduly limit the scope of the invention as stated in the claims. In addition, all of the elements described in connection with the following embodiments should not necessarily be taken as essential requirements of the invention.

1. Distortion Measurement Specimen

Figure 2:
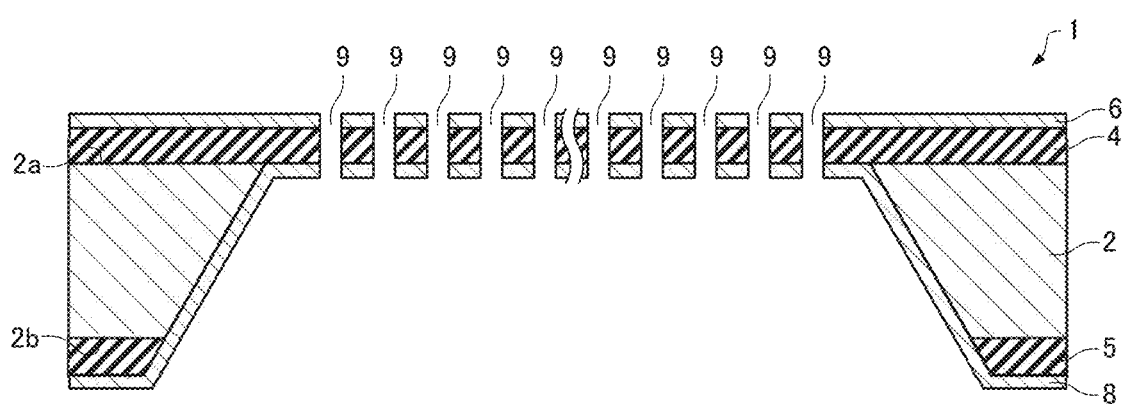
FIG. 2 is a sectional view schematically illustrating a distortion measurement specimen according to an embodiment of the invention.

First, a distortion measurement specimen 1 according to an embodiment of the invention will be described. FIG. 1 is a plan view schematically illustrating the distortion measurement specimen 1. FIG. 2 is a sectional view schematically illustrating the distortion measurement specimen 1. Note that FIG. 2 is a sectional view taken along line II-II in FIG. 1.

The distortion measurement specimen 1 is a specimen for measuring a distortion of an electron microscope image. A distortion measurement method for an electron microscope image using the distortion measurement specimen 1 will be described later.

As illustrated in FIGS. 1 and 2, the distortion measurement specimen 1 includes a substrate 2, a pattern-formed layer 4, a conductive layer 6, and a conductive layer 8.

The substrate 2 is, for example, a silicon substrate. The substrate 2 supports the pattern-formed layer 4. The substrate 2 has a thickness of, for example, around 200 μm.

The pattern-formed layer 4 is formed on the substrate 2. The pattern-formed layer 4 is formed on a first surface 2a (an upper surface) of the substrate 2. Moreover, a layer 5 made of a same material as the pattern-formed layer 4 may be formed on a second surface 2b (a surface on an opposite side to the first surface 2a, a lower surface) of the substrate 2.

The pattern-formed layer 4 has a pattern formed by arranging a plurality of through-holes 9 in a lattice. The through-holes 9 are arranged in a lattice at regular intervals. In other words, the through-holes 9 are arranged in a square lattice. It should be noted that the pattern formed on the pattern-formed layer 4 is not particularly limited as long as the pattern is formed by arranging the through-holes 9 in a lattice. For example, the through-holes 9 may be arranged in a rectangular lattice, a hexagonal lattice, or a rhombic lattice. The through-holes 9 need only be periodically arranged in two predetermined directions.

The through-holes 9 are holes penetrating the pattern-formed layer 4 and, in the illustrated example, the through-holes 9 penetrate the pattern-formed layer 4, the conductive layer 6, and the conductive layer 8. As illustrated in FIG. 1, the through-holes 9 have a circular shape as viewed from a thickness direction of the pattern-formed layer 4 (in a plan view). It should be noted that a planar shape of the through-holes 9 is not limited to a circle and may be a rectangle, a triangle, or other polygons.

The pattern-formed layer 4 is, for example, a silicon nitride layer. Alternatively, the pattern-formed layer 4 may be an oxide layer (for example, a silicon oxide layer) or a metallic layer. In addition, the pattern-formed layer 4 may have a structure in which a plurality of layers are stacked. A thickness of the pattern-formed layer 4 is, for example, 30 nm or more and 500 nm or less.

The conductive layer 6 is formed on top of the pattern-formed layer 4. The conductive layer 8 is formed under the pattern-formed layer 4. In other words, the pattern-formed layer 4 is sandwiched by the conductive layer 6 and the conductive layer 8. The conductive layer 6 and the conductive layer 8 do not block the through-holes 9. The conductive layer 6 and the conductive layer 8 are layers for alleviating charging of the pattern-formed layer 4. The conductive layer 6 and the conductive layer 8 are, for example, titanium layers. It should be noted that materials of the conductive layer 6 and the conductive layer 8 are not particularly limited as long as the conductive layer 6 and the conductive layer 8 are layers with conductivity. A thickness of the conductive layer 6 and the conductive layer 8 is, for example, around 20 nm.

Forming the conductive layer 6 and the conductive layer 8 prevents the pattern-formed layer 4 from being charged. Furthermore, a contrast difference between the through-holes 9 and other portions can be increased when observing the distortion measurement specimen 1 with an electron microscope.

As will be described later, since the distortion measurement specimen 1 is manufactured using a semiconductor manufacturing technique, the through-holes 9 arranged in a lattice can be formed with high accuracy. Therefore, the distortion measurement specimen 1 enables a distortion of an electron microscope image to be measured with high accuracy.

2. Method of Manufacturing Distortion Measurement Specimen

Figure 3:
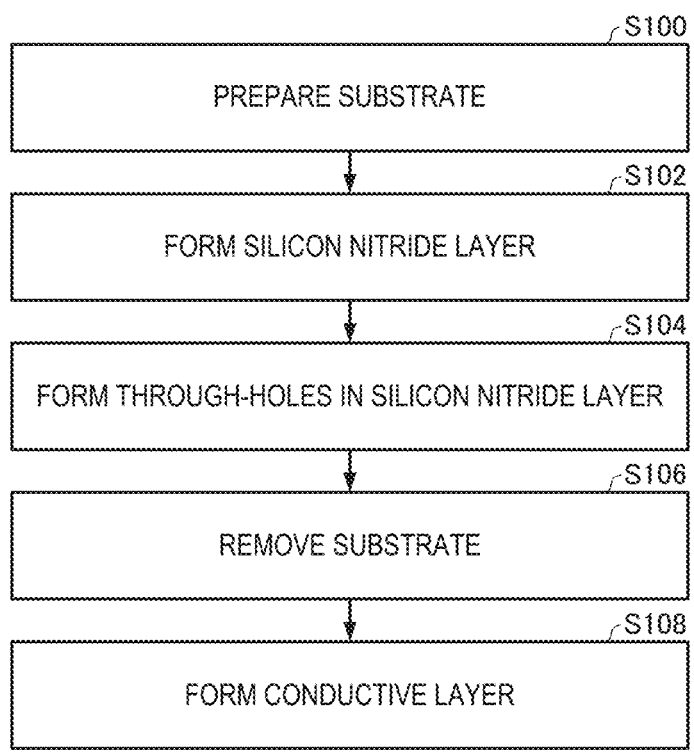
FIG. 3 is a flowchart illustrating an example of a method of manufacturing a distortion measurement specimen according to an embodiment of the invention.

Next, a method of manufacturing the distortion measurement specimen 1 according to an embodiment of the invention will be described below with reference to the drawings. FIG. 3 is a flowchart illustrating an example of a method of manufacturing the distortion measurement specimen 1. FIGS. 4 to 9 are sectional views schematically illustrating a step of manufacturing the distortion measurement specimen 1.

Figure 4:
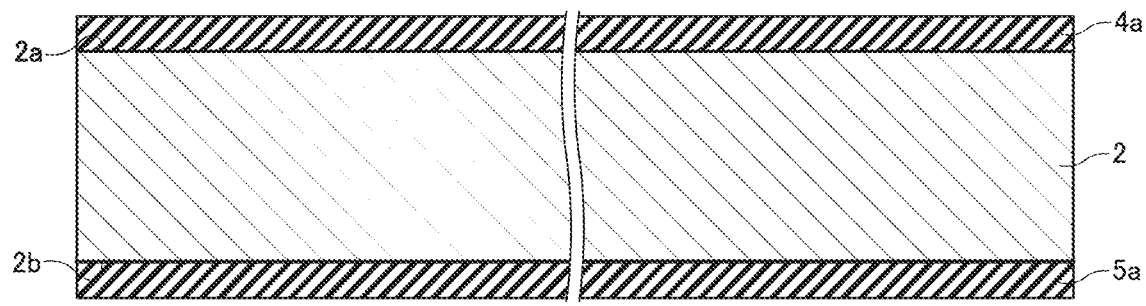
FIG. 4 is a sectional view schematically illustrating a step of manufacturing a distortion measurement specimen according to an embodiment of the invention.

First, as illustrated in FIG. 4, the substrate 2 is prepared (S100).

Next, a silicon nitride layer 4a (the first layer) to become the pattern-formed layer 4 is formed on the first surface 2a of the substrate 2 (S102).

For example, the silicon nitride layer 4a is formed using a low pressure chemical vapor deposition (LPCVD) device which performs deposition in a state of lower pressure than atmospheric pressure. In the present step, deposition is performed so that the silicon nitride layer 4a is imparted with tensile stress. For example, tensile stress can be imparted to the silicon nitride layer 4a by controlling pressure and temperature when performing deposition by the LPCVD device. Since the silicon nitride layer 4a has tensile stress, when removing the substrate 2 and making the silicon nitride layer 4a (the pattern-formed layer 4) a self-supporting film, wrinkles can be prevented from being created on the silicon nitride layer 4a (the pattern-formed layer 4). For example, when forming the silicon nitride layer 4a by sputtering, the silicon nitride layer 4a acquires compressive stress and wrinkles are created when the silicon nitride layer 4a is made a self-supporting film.

In the present step, a mask layer 5a to become a layer 5 illustrated in FIG. 2 is formed on the second surface 2b of the substrate 2 simultaneously with the deposition of the silicon nitride layer 4a. In other words, in the present step, the silicon nitride layer 4a and the mask layer 5a are respectively simultaneously formed on both surfaces of the substrate 2. Alternatively, the deposition of the silicon nitride layer 4a and the deposition of the mask layer 5a may be performed in separate steps.

Next, the through-holes 9 arranged in a lattice are formed on the silicon nitride layer 4a (S104).

Figure 5:
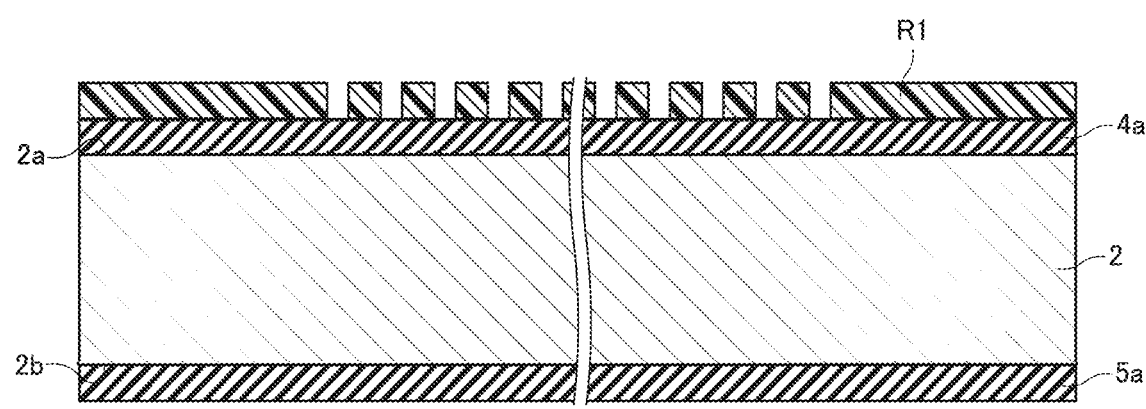
FIG. 5 is a sectional view schematically illustrating a step of manufacturing a distortion measurement specimen according to an embodiment of the invention.

Specifically, as illustrated in FIG. 5, a resist R1 is applied onto the silicon nitride layer 4a, and the resist R1 is exposed and developed to form a mask pattern on the resist R1. For example, exposure (lithography) is performed using an electron-beam lithography system. Performing the exposure using an electron-beam lithography system enables a mask pattern to be formed with high accuracy in the order of nm. Alternatively, the exposure can be performed by laser lithography, UV exposure, and the like in accordance with dimensions of the mask pattern and required accuracy.

Figure 6:
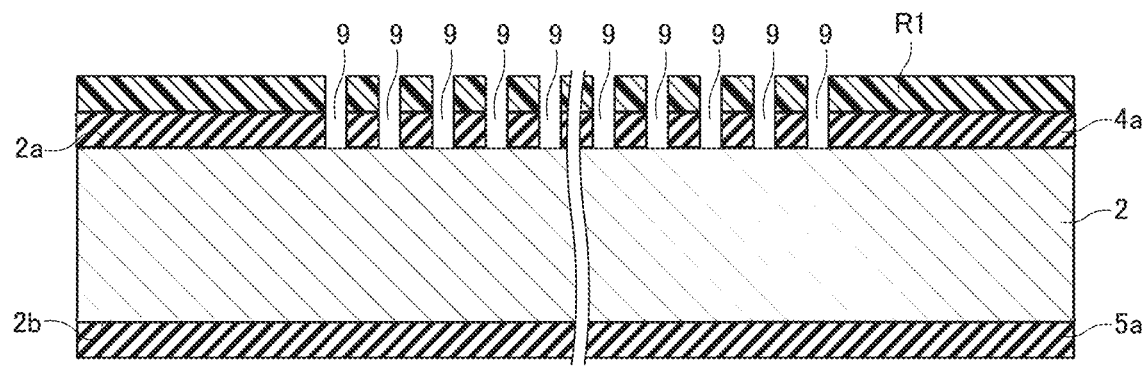
FIG. 6 is a sectional view schematically illustrating a step of manufacturing a distortion measurement specimen according to an embodiment of the invention.

Next, as illustrated in FIG. 6, the silicon nitride layer 4a is etched using the resist R1 as a mask. The etching of the silicon nitride layer 4a is preferably performed by dry etching and more preferably by dry etching using an inductively-coupled plasma etching device. Accordingly, the silicon nitride layer 4a can be accurately patterned. Alternatively, the etching of the silicon nitride layer 4a can be performed by wet etching.

Due to the step described above, the silicon nitride layer 4a (the pattern-formed layer 4) having a pattern in which the through-holes 9 are arranged in a lattice can be formed.

Figure 7:
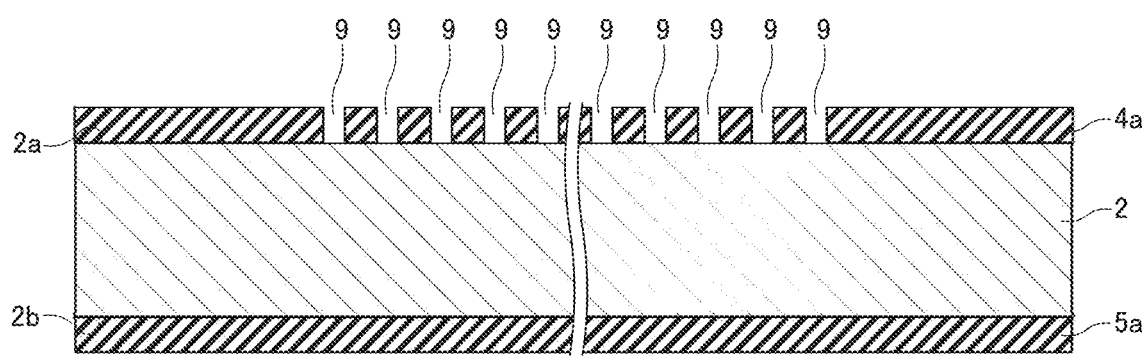
FIG. 7 is a sectional view schematically illustrating a step of manufacturing a distortion measurement specimen according to an embodiment of the invention.

Next, as illustrated in FIG. 7, the resist R1 is removed. The substrate 2 is then removed (S106).

Figure 8:
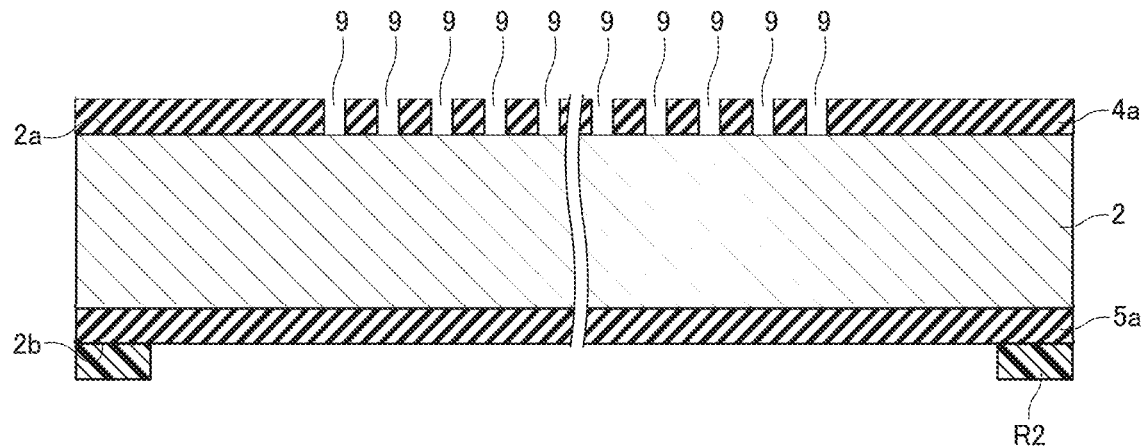
FIG. 8 is a sectional view schematically illustrating a step of manufacturing a distortion measurement specimen according to an embodiment of the invention.
Figure 9:
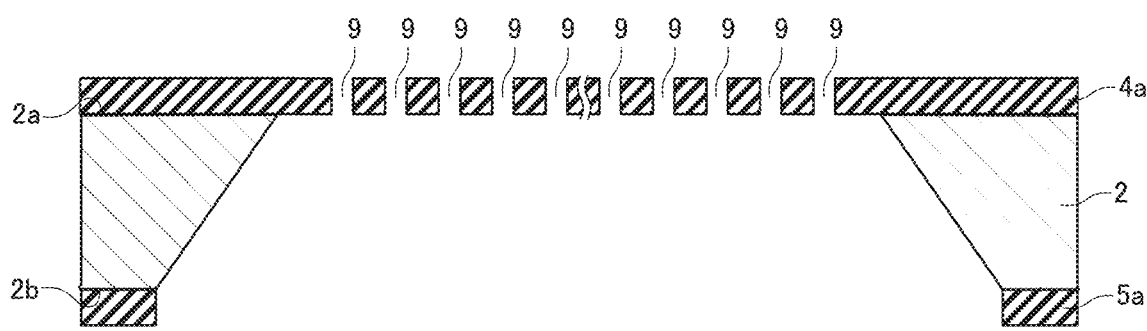
FIG. 9 is a sectional view schematically illustrating a step of manufacturing a distortion measurement specimen according to an embodiment of the invention.

Specifically, first, as illustrated in FIG. 8, a resist R2 is applied onto the mask layer 5a, and the resist R2 is exposed and developed to form a mask pattern on the resist R2. Next, as illustrated in FIG. 9, the mask layer 5a is patterned using the resist R2 as a mask. The resist R2 is then removed, and the second surface 2b of the substrate 2 is etched using the mask layer 5a as a mask.

For example, the etching of the substrate 2 is performed by anisotropic wet etching using potassium hydroxide. Since potassium hydroxide has a high etching rate with respect to the substrate 2 (a silicon substrate) and has an extremely low etching rate with respect to the silicon nitride layer 4a, potassium hydroxide is suitable as an etching solution for the substrate 2. Alternatively, the etching of the substrate 2 can be performed by deep reactive ion etching (deep RIE). In this case, since the silicon nitride layer 4a is etched by deep reactive ion etching, the silicon nitride layer 4a is preferably provided in advance with an etching stop layer (for example, an aluminum layer or a chromium layer) on the side of the substrate 2.

Etching and removing the substrate 2 enables a pattern-formed region of the silicon nitride layer 4a to be exposed. As a result, the silicon nitride layer 4a becomes a self-supporting film. Since the silicon nitride layer 4a is imparted with tensile stress as described above, no wrinkles are created on the silicon nitride layer 4a even when the substrate 2 is removed in the present step.

Next, as illustrated in FIG. 2, the conductive layer 6 (the second layer) is formed on the upper surface of the pattern-formed layer 4 (the silicon nitride layer 4a) and the conductive layer 8 is formed on the lower surface of the pattern-formed layer 4 (the silicon nitride layer 4a) (S108).

Deposition of the conductive layer 6 and the conductive layer 8 is performed by, for example, chemical vapor deposition (CVD), sputtering, or the like. The conductive layer 8 may be formed so as to cover the substrate 2 simultaneously with the deposition of the conductive layer 8. The deposition of the conductive layer 6 and the deposition of the conductive layer 8 may be performed simultaneously. The conductive layer 6 and the conductive layer 8 are formed with such a thickness that prevents the through-holes 9 formed on the silicon nitride layer 4a from being filled.

Due to the steps described above, the distortion measurement specimen 1 can be manufactured.

It should be noted that, while an example in which the pattern-formed layer 4 is a silicon nitride layer has been described above, the distortion measurement specimen 1 can be manufactured in similar steps even when the pattern-formed layer 4 is a layer made of other materials.

In addition, while a case of manufacturing a single distortion measurement specimen 1 has been described above, a plurality of the distortion measurement specimens 1 can also be simultaneously manufactured on a single substrate 2 (a silicon wafer).

For example, the method of manufacturing the distortion measurement specimen 1 has the following features.

The method of manufacturing the distortion measurement specimen 1 includes the steps of: preparing the substrate 2; forming the silicon nitride layer 4a on the first surface 2a of the substrate 2; forming the through-holes 9 arranged in a lattice by patterning the silicon nitride layer 4a; and etching the second surface 2b on an opposite side to the first surface 2a of the substrate 2 to remove the substrate 2. Therefore, with the method of manufacturing the distortion measurement specimen 1, the distortion measurement specimen 1 can be manufactured using a semiconductor manufacturing technique and a pattern made up of the through-holes 9 arranged in a lattice with high accuracy (positional accuracy and dimensional accuracy) can be formed. As a result, a distortion measurement specimen which enables a measurement of a distortion of an electron microscope image to be performed with high accuracy can be manufactured.

With the method of manufacturing the distortion measurement specimen 1, in the step of forming the through-holes 9 by patterning the silicon nitride layer 4a, the resist R1 for patterning the silicon nitride layer 4a is exposed by an electron-beam lithography system. Accordingly, through-holes 9 arranged in a lattice with high accuracy (for example, accuracy in the order of nm) can be formed. Therefore, a distortion measurement specimen which enables a measurement of a distortion of an electron microscope image to be performed with high accuracy can be manufactured.

With the method of manufacturing the distortion measurement specimen 1, in the step of forming the through-holes 9 by patterning the silicon nitride layer 4a, etching of the silicon nitride layer 4a is performed using an inductively-coupled plasma etching device. Accordingly, through-holes 9 arranged in a lattice with high accuracy (for example, accuracy in the order of nm) can be formed. Therefore, a distortion measurement specimen which enables a measurement of a distortion of an electron microscope image to be performed with high accuracy can be manufactured.

With the method of manufacturing the distortion measurement specimen 1, in the step of forming the silicon nitride layer 4a, the silicon nitride layer 4a is formed so that the silicon nitride layer 4a is imparted with tensile stress. Accordingly, wrinkles can be prevented from being created on the silicon nitride layer 4a even when the substrate 2 is removed.

With the method of manufacturing the distortion measurement specimen 1, the shape of the through-holes 9 as viewed from a thickness direction of the silicon nitride layer 4a is a circle. Therefore, the through-holes 9 can be formed with accuracy. Since a size of the through-hole 9 is minute, when a planar shape of the through-holes 9 is a rectangle or a polygon, it is difficult to form corners of the through-holes 9 with accuracy. By making the planar shape of the through-holes 9 a circle without any corners, the through-holes 9 can be formed with greater accuracy as compared to cases where the planar shape is a rectangle or a polygon.

Figure 10:
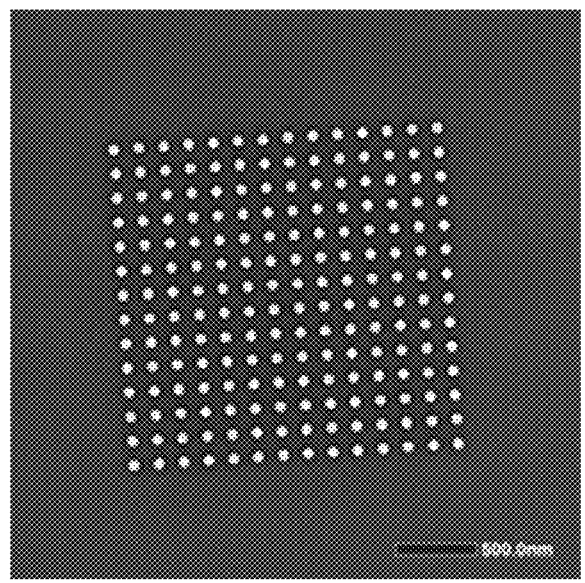
FIG. 10 is a transmission electron microscope image of a distortion measurement specimen manufactured by a method of manufacturing a distortion measurement specimen according to an embodiment of the invention.
Figure 11:
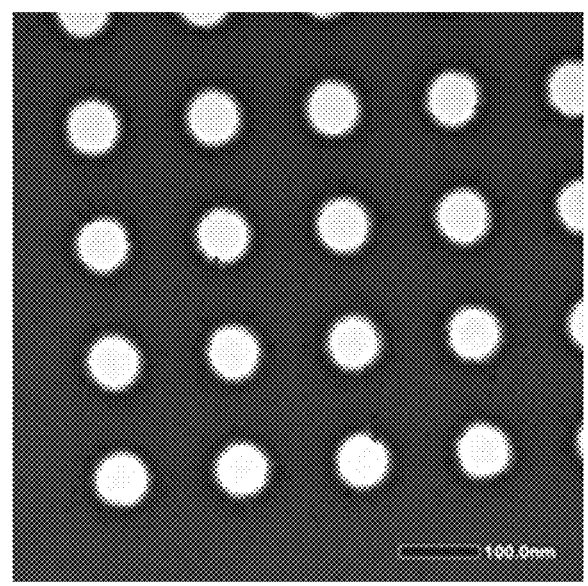
FIG. 11 is a transmission electron microscope image of a distortion measurement specimen manufactured by a method of manufacturing a distortion measurement specimen according to an embodiment of the invention.

FIGS. 10 and 11 are transmission electron microscope images (TEM images) of a distortion measurement specimen manufactured by the method of manufacturing a distortion measurement specimen according to an embodiment of the invention.

Manufacturing conditions of the distortion measurement specimen illustrated in FIGS. 10 and 11 are as follows.

A silicon substrate with a thickness of 200 μm was used as the substrate 2. A silicon nitride layer with a thickness of 100 nm was used as the pattern-formed layer 4. The electron-beam lithography system JBX-6300FS (manufactured by JEOL Ltd.) was used for exposure (lithography) of the resist R1. In addition, the inductively coupled plasma (ICP) etching device RIE-400iP (manufactured by Samco Inc.) was used for etching of the pattern-formed layer 4. Using these devices, a pattern arranging through-holes 9 with a diameter of 60 nm in a square lattice at a pitch of 150 nm was formed on the pattern-formed layer 4. The through-holes 9 were given a circular planar shape.

The etching of the substrate 2 was performed by anisotropic wet etching using potassium hydroxide. In addition, a titanium layer with a thickness of 20 nm was respectively used for the conductive layer 6 and the conductive layer 8. In other words, the distortion measurement specimen was given a layered structure constituted by a titanium layer (20 nm)/a silicon nitride layer (100 nm)/a titanium layer (20 nm).

The distortion measurement specimen manufactured in this manner was photographed using the transmission electron microscope JEM-2200FS (manufactured by JEOL Ltd.) to acquire the TEM images illustrated in FIGS. 10 and 11.

As illustrated in FIGS. 10 and 11, in the manufactured distortion measurement specimen, a pattern constituted by through-holes 9 arranged in a lattice is formed with accuracy in the order of nm. In addition, the formed pattern coincided, with high accuracy, with a computer-aided design (CAD) screen used by the electron-beam lithography system. Furthermore, as illustrated in FIGS. 10 and 11, no wrinkles are observed in the pattern-formed layer 4 (the silicon nitride layer).

3. Distortion Measurement Method for Electron Microscope Image

3.1. First Embodiment

Next, a distortion measurement method for an electron microscope image according to a first embodiment will be described. With the distortion measurement method for an electron microscope image according to the first embodiment, a measurement of a distortion is performed using the distortion measurement specimen 1.

Figure 12:
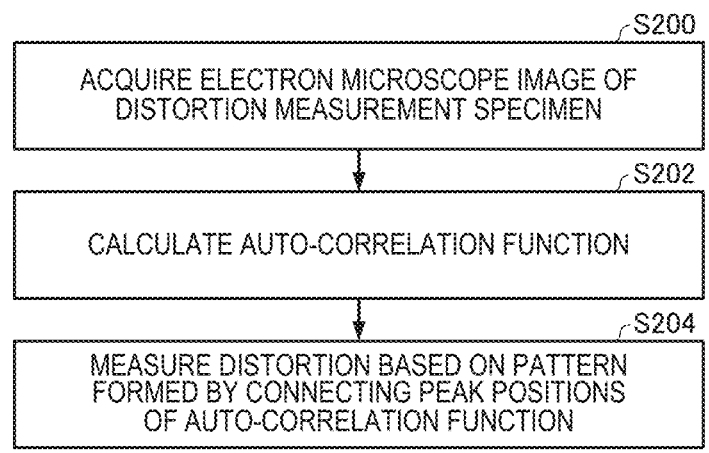
FIG. 12 is a flowchart illustrating an example of a distortion measurement method for an electron microscope image according to the first embodiment.

FIG. 12 is a flowchart illustrating an example of the distortion measurement method for an electron microscope image according to the first embodiment.

The distortion measurement method for an electron microscope image according to the first embodiment includes the steps of: acquiring an electron microscope image of a distortion measurement specimen (S200); calculating an auto-correlation function of the electron microscope image of the distortion measurement specimen (S202); and measuring the distortion of the electron microscope image based on a pattern formed by connecting peak positions of the calculated auto-correlation function (S204).

(1) Step of Acquiring Electron Microscope Image (S200)

First, the distortion measurement specimen 1 is loaded to an electron microscope to photograph an electron microscope image of the distortion measurement specimen 1, and an electron microscope image of the distortion measurement specimen 1 is acquired. A case where the electron microscope is a transmission electron microscope will now be described.

The distortion measurement specimen 1 is loaded to a specimen plane (a specimen stage) of the transmission electron microscope or to a plane conjugate to the specimen plane. With the distortion measurement method for an electron microscope image according to the first embodiment, a distortion of a transmission electron microscope image (a TEM image) by optical systems (an electron lens and the like) in a stage subsequent to a position where the distortion measurement specimen 1 is loaded can be measured.

Figure 13:
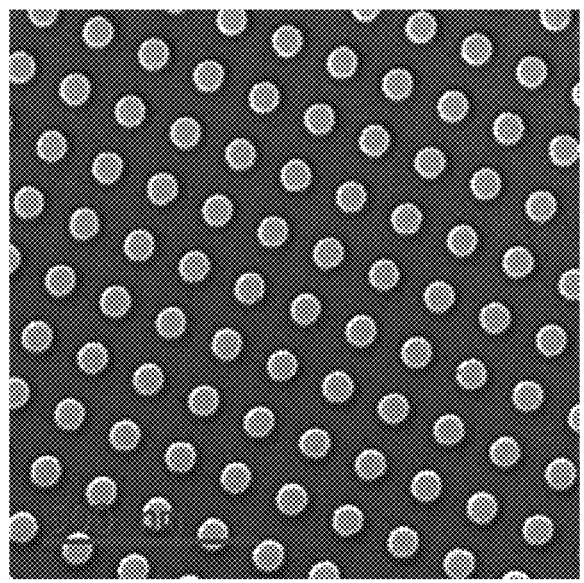
FIG. 13 is a TEM image of a distortion measurement specimen.

FIG. 13 is a TEM image obtained by photographing the distortion measurement specimen 1 illustrated in FIGS. 10 and 11 at an observation magnification power of 30,000×. Hereinafter, the distortion measurement method for an electron microscope image according to the first embodiment will be described using the TEM image illustrated in FIG. 13.

(2) Step of Calculating Auto-Correlation Function (S202)

Next, an auto-correlation function (a two-dimensional auto-correlation function) of the TEM image acquired in the step of acquiring an electron microscope image (S200) is calculated. By calculating the auto-correlation function of an electron microscope image, a pattern (an auto-correlation pattern) reflecting a periodicity of the pattern formed by the through-holes 9 arranged in a lattice is obtained. Alternatively, a low pass filter process may be performed before calculating the auto-correlation function. Accordingly, noise of the TEM image can be reduced.

Figure 14:
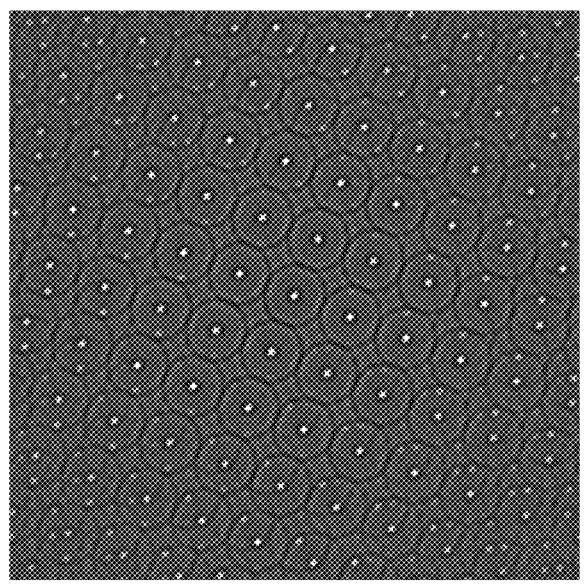
FIG. 14 is a diagram illustrating an auto-correlation function of a TEM image.

FIG. 14 is a diagram illustrating an auto-correlation function of the TEM image illustrated in FIG. 13.

A plurality of peaks are observed in the auto-correlation function of the TEM image illustrated in FIG. 14, and intervals of the peaks correspond to intervals of the through-holes 9.

(3) Step of Measuring Distortion of Electron Microscope Image (S204)

Next, a distortion of the TEM image is measured based on the calculated auto-correlation function. The measurement of the distortion of the TEM image is performed by measuring a distortion of an ellipse having, as an origin, a center formed by connecting peak positions of the auto-correlation function illustrated in FIG. 14.

FIG. 15 is a diagram for illustrating a method of extracting an ellipse from an auto-correlation function.

As illustrated in FIG. 15, four peak positions most adjacent to an origin of the auto-correlation function are extracted, and a circle which includes the four peak positions and which has a width centered on the origin is adopted as a first circle. Next, a circle having a radius that is $\sqrt{2}$ times a radius of the first circle is adopted as a second circle, and four peak positions in the neighborhood of the second circle are extracted. In a similar manner, a circle having a radius that is 2 times the radius of the first circle is adopted as a third circle, and four peak positions in the neighborhood of the third circle are extracted. In a similar manner, a circle having a radius that is $2\sqrt{2}$ times the radius of the first circle is adopted as a fourth circle, and four peak positions in the neighborhood of the fourth circle are extracted.

FIG. 15 includes coordinates of the peak positions extracted in this manner, four ellipses obtained from four peak positions respectively in the neighborhood of the first to fourth circles, and average radii calculated from averages of major axes and minor axes of the ellipses.

Figure 16:
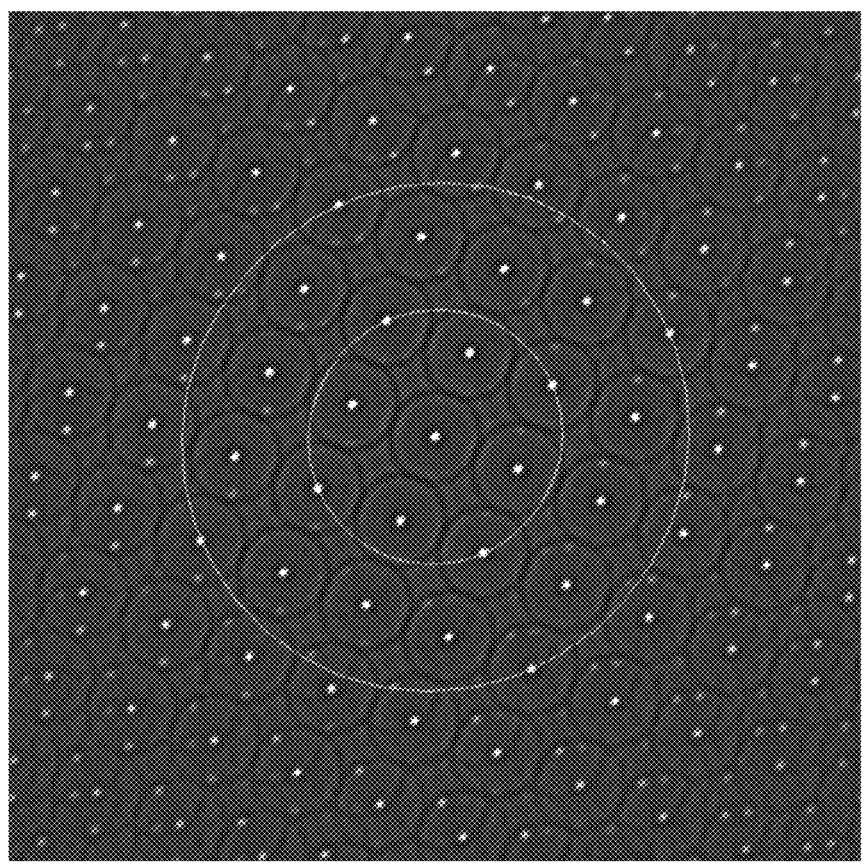
FIG. 16 is a diagram illustrating a method of measuring a distortion of a TEM image from an ellipse formed by connecting peak positions of an auto-correlation function.

FIG. 16 is a diagram for illustrating a method of measuring a distortion of a TEM image from an ellipse formed by connecting peak positions of an auto-correlation function.

As illustrated in FIG. 16, an ellipse is drawn from positions obtained by respectively multiplying the four peak positions extracted from the first circle by $\sqrt{2}$ and the four peak positions extracted from the second circle. For example, an ellipse can be drawn by fitting an ellipse to these eight points. When the origin of the auto-correlation function is denoted by (0, 0) and coordinates of a peak position are denoted by (X, Y), a position obtained by multiplying the peak position by $\sqrt{2}$ is denoted by coordinates ($\sqrt{2} \times X$, $\sqrt{2} \times Y$).

In a similar manner, an ellipse is drawn from positions obtained by respectively multiplying the four peak positions extracted from the neighborhood of the third circle by $\sqrt{2}$ and the four peak positions extracted from the fourth circle. As a result, an ellipse having the origin illustrated in FIG. 16 as its center is obtained.

The ellipse is expressed by a function $(Ax+By)^2+(Bx+Cy)^2=1$, and aspect ratios in respective directions are calculated from A, B, and C.

Figure 17:
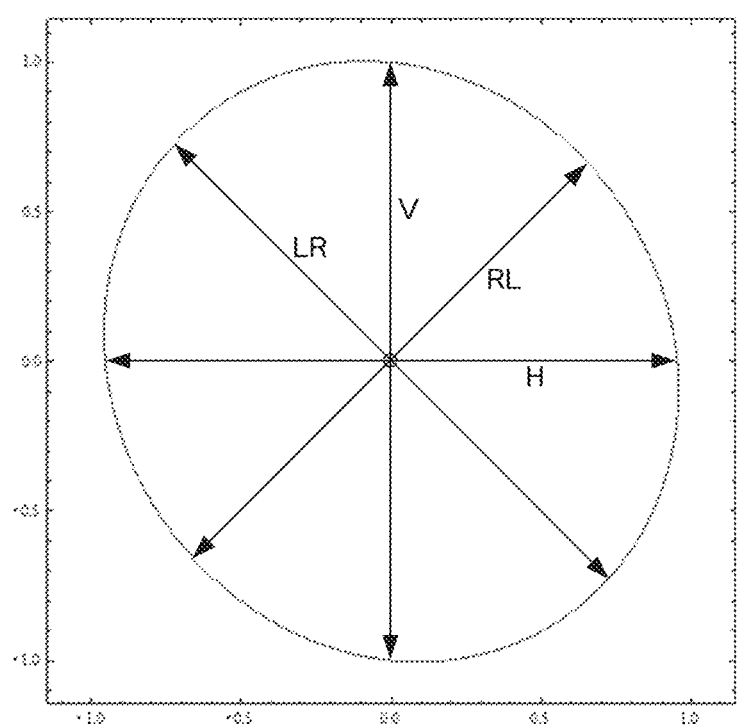
FIG. 17 is a diagram illustrating directions of an ellipse.

FIG. 17 is a diagram illustrating the respective directions of an ellipse.

V (Vertical), H (Horizontal), LR (Upper Left-Lower Right), and RL (Upper Right-Lower Left) are defined as illustrated in FIG. 17.

FIGS. 18 to 22 are diagrams for illustrating elliptic parameters A, B, and C.

Figure 18:
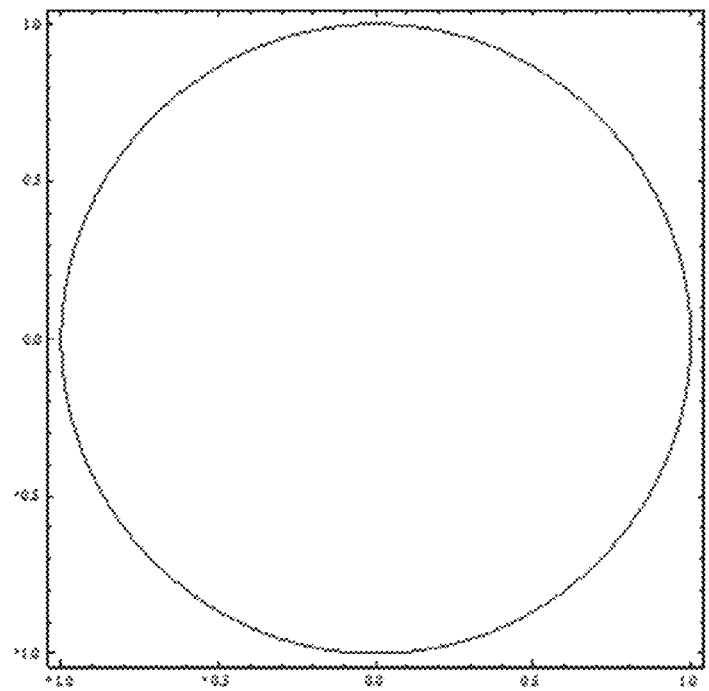
FIG. 18 is a diagram illustrating elliptic parameters A, B, and C.
Figure 19:
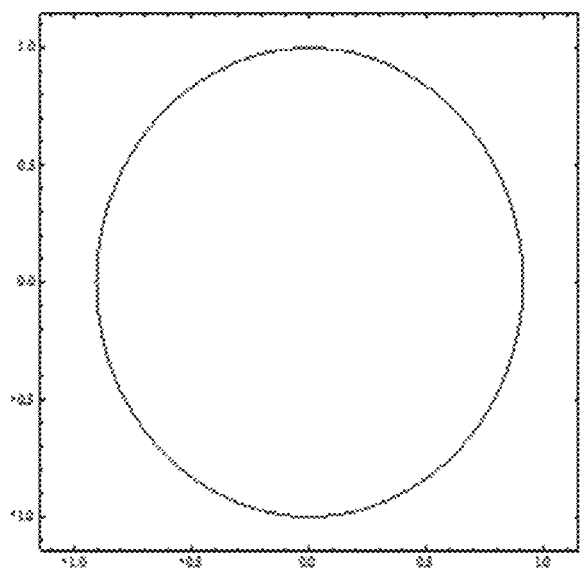
FIG. 19 is a diagram illustrating elliptic parameters A, B, and C.
Figure 20:
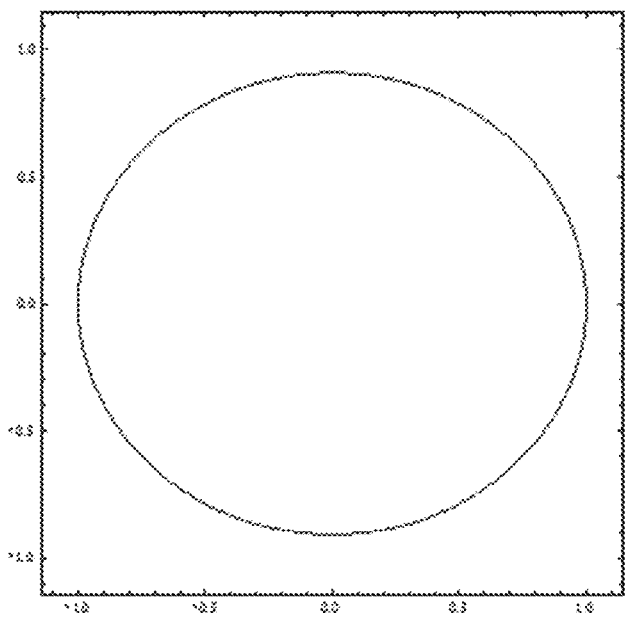
FIG. 20 is a diagram illustrating elliptic parameters A, B, and C.

In expression $(Ax+By)^2+(Bx+Cy)^2=1$, a true circle is obtained when A=1, B=0, and C=1 (refer to FIG. 18). In addition, a vertical to horizontal ratio of V/H=1/0.9=1.111 is obtained when A=1.1, B=0, and C=1 (refer to FIG. 19). Furthermore, a vertical to horizontal ratio of V/H=0.9/1=0.9 is obtained when A=1, B=0, and C=1.1 (refer to FIG. 20). From the above, the vertical to horizontal ratio V/H is represented by expression (1) below.

$$\frac{V}{H} = \frac{1/C}{1/A} = \frac{A}{C} \tag{1}$$

Figure 21:
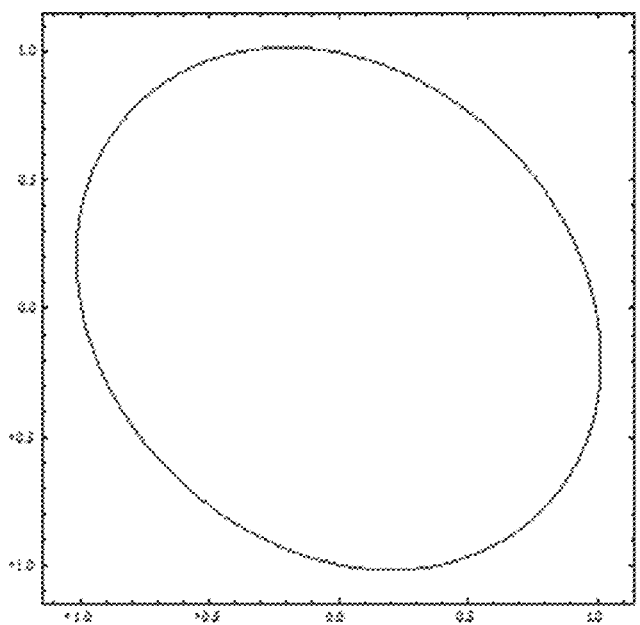
FIG. 21 is a diagram illustrating elliptic parameters A, B, and C.
Figure 22:
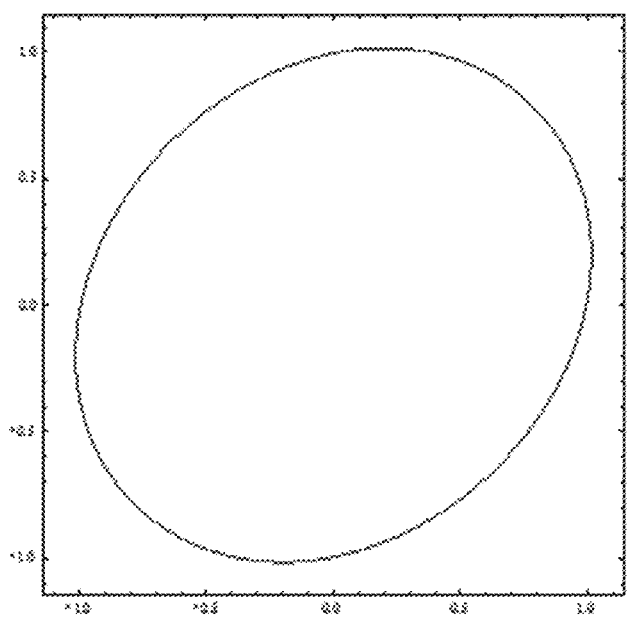
FIG. 22 is a diagram illustrating elliptic parameters A, B, and C.

In addition, in expression $(Ax+By)^2+(Bx+Cy)^2=1$, a diagonal ratio LR/RL=1.103/0.905=1.22 is obtained when A=1, B=0.1, and C=1 (refer to FIG. 21). Furthermore, a diagonal ratio LR/RL=0.905/1.103=0.82 is obtained when A=1, B=−0.1, and C=1 (refer to FIG. 22).

When B is sufficiently small, the diagonal ratio LR/RL is represented by expression (2) below.

$$\frac{LR}{RL} = 1 + \frac{2B}{(A+C)/2} \tag{2}$$

Aspect ratios obtained from an inner ellipse among the two ellipses illustrated in FIG. 16 calculated using expressions (1) and (2) above are as follows.

Vertical to horizontal ratio V/H=100.23

Diagonal ratio LR/RL=97.8148

In a similar manner, aspect ratios obtained from an outer ellipse among the two ellipses illustrated in FIG. 16 are as follows.

Vertical to horizontal ratio V/H=100.217

Diagonal ratio LR/RL=97.8109

As described above, the aspect ratios of the inner ellipse and the aspect ratios of the outer ellipse are similar values, which indicates that aspect ratios of a TEM image can be accurately calculated.

Due to the steps described above, a distortion of a TEM image can be measured.

With the distortion measurement method for an electron microscope image according to the first embodiment, a distortion (aspect ratios (a vertical to horizontal ratio and a diagonal ratio)) of the TEM image can be measured.

It should be noted that, while a distortion has been measured based on concentric ellipses formed by connecting peak positions of an auto-correlation function, a distortion may be measured from one ellipse.

In addition, a pattern formed by connecting peak positions of an auto-correlation function is not limited to an ellipse or concentric ellipses and may be another pattern such as a rectangle or a polygon. Even in such cases, a distortion can be measured in a similar manner to an ellipse or concentric ellipses.

For example, the distortion measurement method for an electron microscope image according to the first embodiment has the following features.

With the distortion measurement method for an electron microscope image according to the first embodiment, a distortion of an electron microscope image is measured using an electron microscope image of a distortion measurement specimen manufactured by the method of manufacturing a distortion measurement specimen described above. With the method of manufacturing a distortion measurement specimen described above, a pattern made up of the through-holes 9 arranged in a lattice with high accuracy can be formed. Therefore, with the distortion measurement method according to the first embodiment, a distortion of an electron microscope image can be accurately measured.

With the distortion measurement method for an electron microscope image according to the first embodiment, an auto-correlation function of an electron microscope image of the distortion measurement specimen 1 having through-holes 9 arranged in a lattice is calculated, and a distortion of the electron microscope image is measured based on a pattern formed by connecting peak positions of the auto-correlation function. Therefore, a distortion of an electron microscope image can be readily and accurately measured.

With the distortion measurement method for an electron microscope image according to the first embodiment, a pattern formed by connecting peak positions of the auto-correlation function is an ellipse. Therefore, a distortion of an electron microscope image can be readily and accurately measured. In addition, by adopting concentric ellipses as the pattern formed by connecting peak positions of the auto-correlation function, a distortion of an electron microscope image can be measured with higher accuracy.

3.2. Second Embodiment

Figure 23:
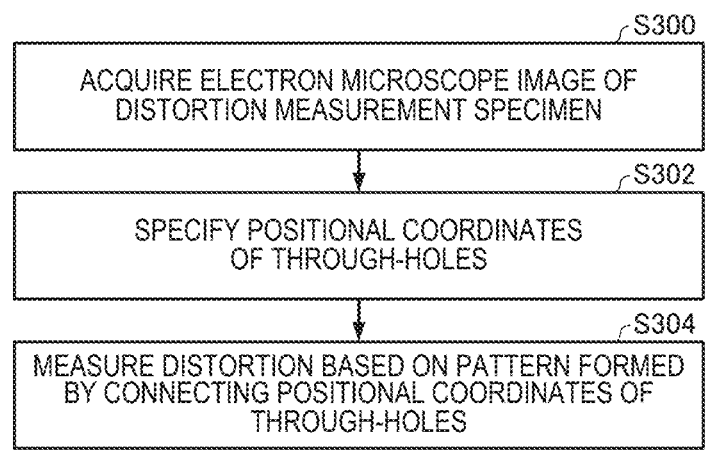
FIG. 23 is a flowchart illustrating an example of a distortion measurement method for an electron microscope image according to the second embodiment.

Next, a distortion measurement method for an electron microscope image according to a second embodiment will be described. FIG. 23 is a flowchart illustrating an example of the distortion measurement method for an electron microscope image according to the second embodiment. The following description will focus on points that differ from the distortion measurement method for an electron microscope image according to the first embodiment described above, and a description of similar points will be omitted.

The distortion measurement method for an electron microscope image according to the second embodiment includes the steps of: acquiring an electron microscope image of a distortion measurement specimen (S300); specifying positional coordinates of the through-holes 9 on the electron microscope image of the distortion measurement specimen (S302); and measuring the distortion of the electron microscope image based on a pattern formed by connecting the positional coordinates of the through-holes 9 (S304).

In the second embodiment, a distortion of an electron microscope image can be measured more simply by using an image recognition technique. Hereinafter, an example will be described in which OpenCV that is a library of functions related to image recognition is used to measure a distortion of an electron microscope image.

(1) Step of Acquiring Electron Microscope Image (S300)

The present step is performed in a similar manner to the acquisition of an electron microscope image (S200) in the first embodiment described above.

(2) Step of Specifying Positional Coordinates of Through-Holes (S302)

Next, the positional coordinates of the through-holes 9 on the electron microscope image acquired in the step of acquiring an electron microscope image (S300) are specified.

Figure 24:
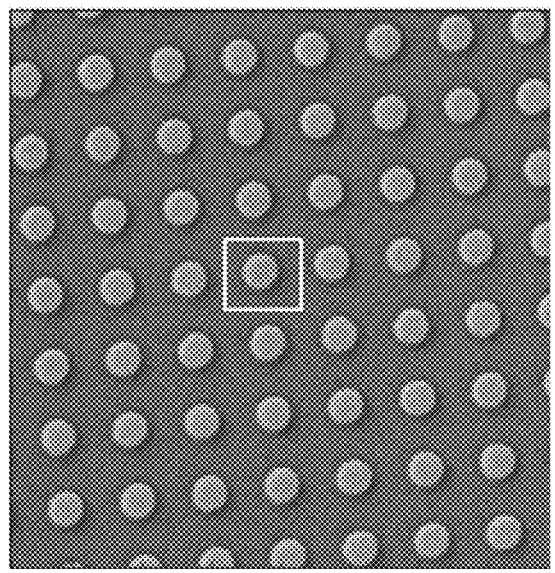
FIG. 24 is a TEM image acquired in a step of acquiring an electron microscope image.

FIG. 24 is a TEM image acquired in the step of acquiring an electron microscope image (S300). FIGS. 25 to 30 are diagrams for illustrating a step of specifying positional coordinates of the through-holes 9.

Figure 25:
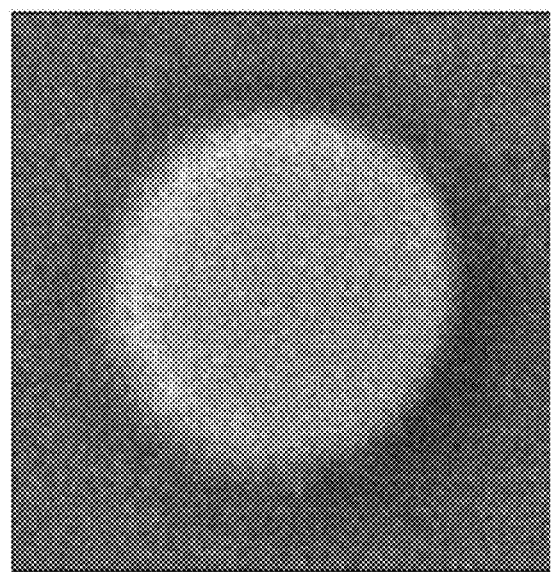
FIG. 25 is a diagram illustrating a step of specifying positional coordinates of a through-hole.
Figure 26:
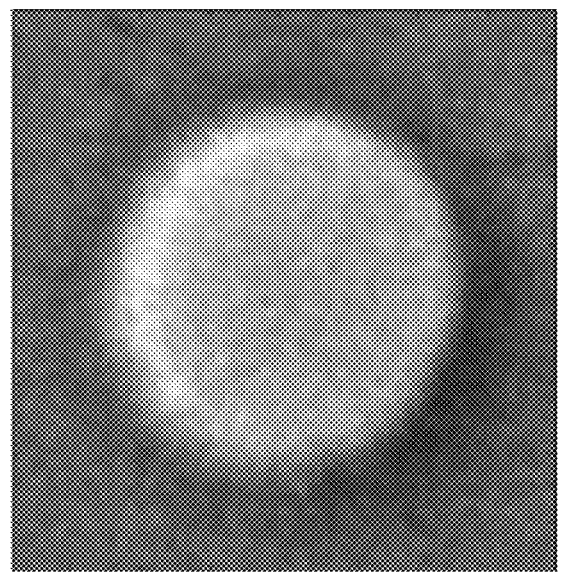
FIG. 26 is a diagram illustrating a step of specifying positional coordinates of a through-hole.

First, the TEM image is blurred. FIG. 25 is a diagram illustrating an enlargement of a region enclosed by a square on the TEM image illustrated in FIG. 24, and FIG. 26 is a diagram obtained by blurring FIG. 25.

Figure 27:
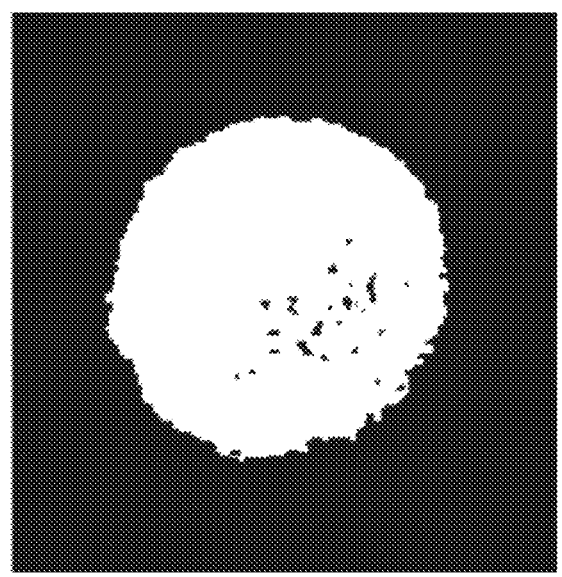
FIG. 27 is a diagram illustrating a step of specifying positional coordinates of a through-hole.
Figure 28:
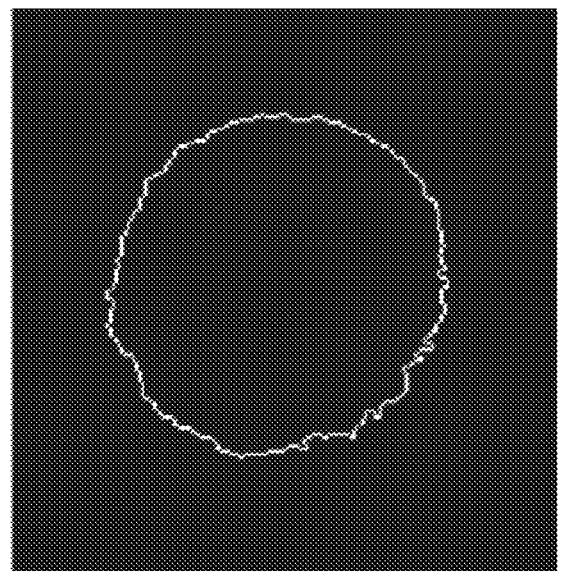
FIG. 28 is a diagram illustrating a step of specifying positional coordinates of a through-hole.
Figure 29:
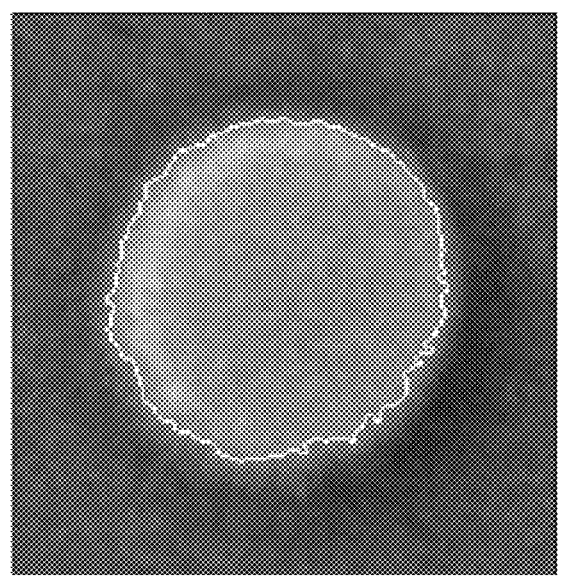
FIG. 29 is a diagram illustrating a step of specifying positional coordinates of a through-hole.

Next, as illustrated in FIG. 27, the blurred TEM image is binarized. Next, as illustrated in FIG. 28, a contour of an image of one of the through-holes 9 is detected. FIG. 29 is a diagram in which the detected contour is drawn on top of the original TEM image (refer to FIG. 25).

Figure 30:
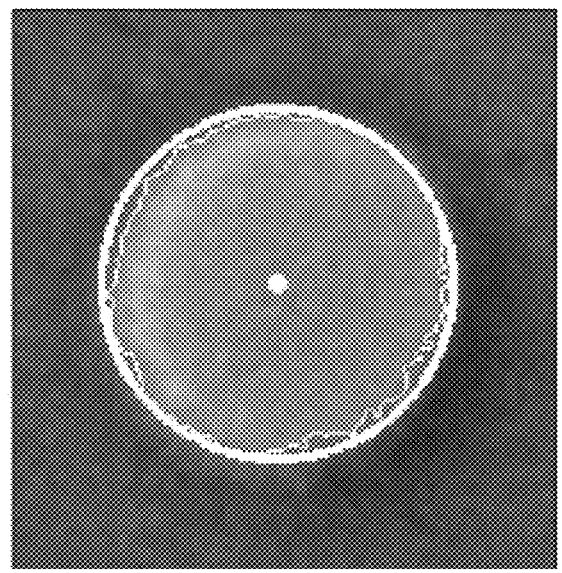
FIG. 30 is a diagram illustrating a step of specifying positional coordinates of a through-hole.

Next, as illustrated in FIG. 30, a smallest circle enclosing the detected contour is detected. Positional coordinates of a center of the smallest circle are adopted as positional coordinates of the through-hole 9. In FIG. 30, the smallest circle enclosing the contour of the through-hole 9 and the center of the smallest circle are drawn on the TEM image illustrated in FIG. 25.

It should be noted that although an example has been described in which a smallest circle enclosing the contour of the through-hole 9 is detected and positional coordinates of the through-hole 9 are specified, a method thereof is not particularly limited as long as the positional coordinates of the through-hole 9 on the TEM image can be specified. For example, the positional coordinates of the through-hole 9 can be similarly specified by detecting a center of gravity of the contour of the through-hole 9.

(3) Step of Measuring Distortion of Electron Microscope Image (S304)

Next, a distortion of a TEM image is measured based on a pattern formed by connecting the positional coordinates of the through-holes 9 on the TEM image. In the second embodiment, a distortion of a TEM image is measured by fitting a grid pattern to a pattern formed by connecting the positional coordinates of the through-holes 9.

Figure 31:
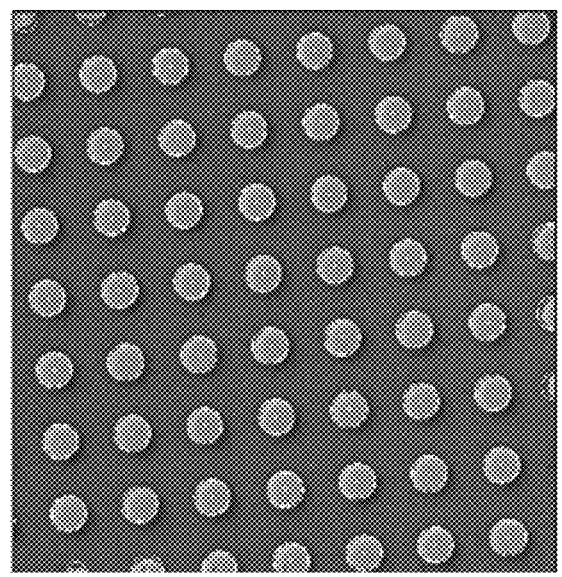
FIG. 31 is a diagram illustrating a step of measuring a distortion of a TEM image.
Figure 32:
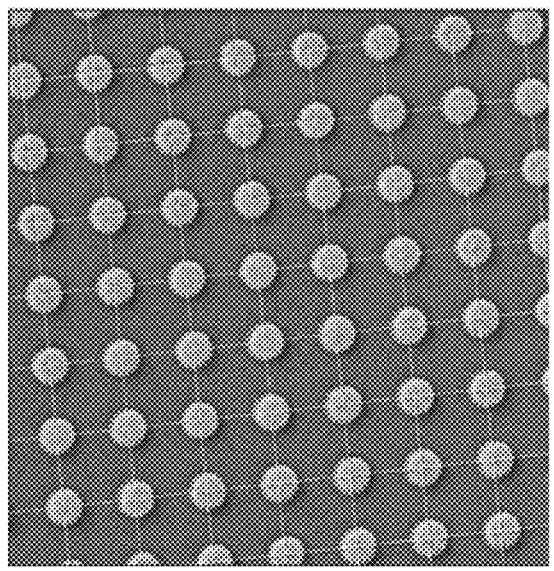
FIG. 32 is a diagram illustrating a step of measuring a distortion of a TEM image.

FIGS. 31 and 32 are diagrams for illustrating a step of measuring a distortion of a TEM image.

Specifically, first, as illustrated in FIG. 31, images of through-holes 9 at edges of the TEM image which are not entirely included in the TEM image are excluded. This is done because, when an entire through-hole 9 is not included, positional coordinates of the through-hole 9 cannot be accurately specified. Next, as illustrated in FIG. 32, a grid pattern is fitted to a pattern formed by connecting the positional coordinates of the through-holes 9. Fitting is performed by distorting a square grid pattern so as to minimize distances between intersections of the grid pattern and positional coordinates of the through-holes 9. The distortion of the grid pattern at this point corresponds to a distortion of the TEM image. Therefore, the distortion of the TEM image can be determined from a distortion value of the grid pattern when the grid pattern is fitted.

As illustrated in FIG. 32, fitting a grid pattern to a pattern formed by connecting the positional coordinates of the through-holes 9 resulted in $Y/X=0.997$ and $Y2/X2=0.987$, where $Y/X$ denotes a vertical to horizontal ratio and $Y2/X2$ denotes a diagonal ratio.

Due to the steps described above, a distortion of a TEM image can be measured.

With the distortion measurement method for an electron microscope image according to the second embodiment, a high-order distortion such as a barrel distortion and a pin-cushion distortion can be measured in addition to an aspect ratio (a linear distortion) as the distortion of a TEM image.

It should be noted that, while a distortion is measured by fitting a grid pattern to a pattern formed by connecting the positional coordinates of the through-holes 9 in the description given above, a pattern to be fitted to a pattern formed by connecting the positional coordinates of the through-holes 9 is not particularly limited.

For example, the distortion measurement method for an electron microscope image according to the second embodiment has the following features.

With the distortion measurement method for an electron microscope image according to the second embodiment, a distortion of an electron microscope image is measured using an electron microscope image of a distortion measurement specimen manufactured by the method of manufacturing a distortion measurement specimen described above. Therefore, with the distortion measurement method according to the second embodiment, a distortion of an electron microscope image can be accurately measured.

With the distortion measurement method for an electron microscope image according to the second embodiment, a through-hole 9 and a periphery thereof are separated by binarization in order to specify positional coordinates of the through-hole 9. Therefore, accurately measuring a distortion requires a contrast difference between the through-hole 9 and a periphery thereof. In the second embodiment, since the distortion measurement specimen 1 manufactured by the method of manufacturing a distortion measurement specimen described above is used, the through-holes 9 can be formed with accuracy using a semiconductor manufacturing technique. Therefore, an electron microscope image with a large contrast difference between the through-holes 9 and peripheries thereof can be obtained and a distortion of the electron microscope image can be measured with accuracy.

With the distortion measurement method for an electron microscope image according to the second embodiment, positional coordinates of the through-holes 9 on an electron microscope image of the distortion measurement specimen 1 are specified, and a distortion of the electron microscope image is measured based on a pattern formed by connecting the positional coordinates. Therefore, a distortion of an electron microscope image can be readily and accurately measured.

With the distortion measurement method for an electron microscope image according to the second embodiment, in the step of measuring a distortion, the distortion is calculated by fitting a grid pattern to a pattern formed by connecting the positional coordinates of the through-holes 9. Therefore, the distortion measurement method for an electron microscope image according to the second embodiment is not limited to measuring an aspect ratio (a linear distortion) and is also capable of measuring high-order distortions.

4. Electron Microscope

4.1. First Embodiment

Figure 33:
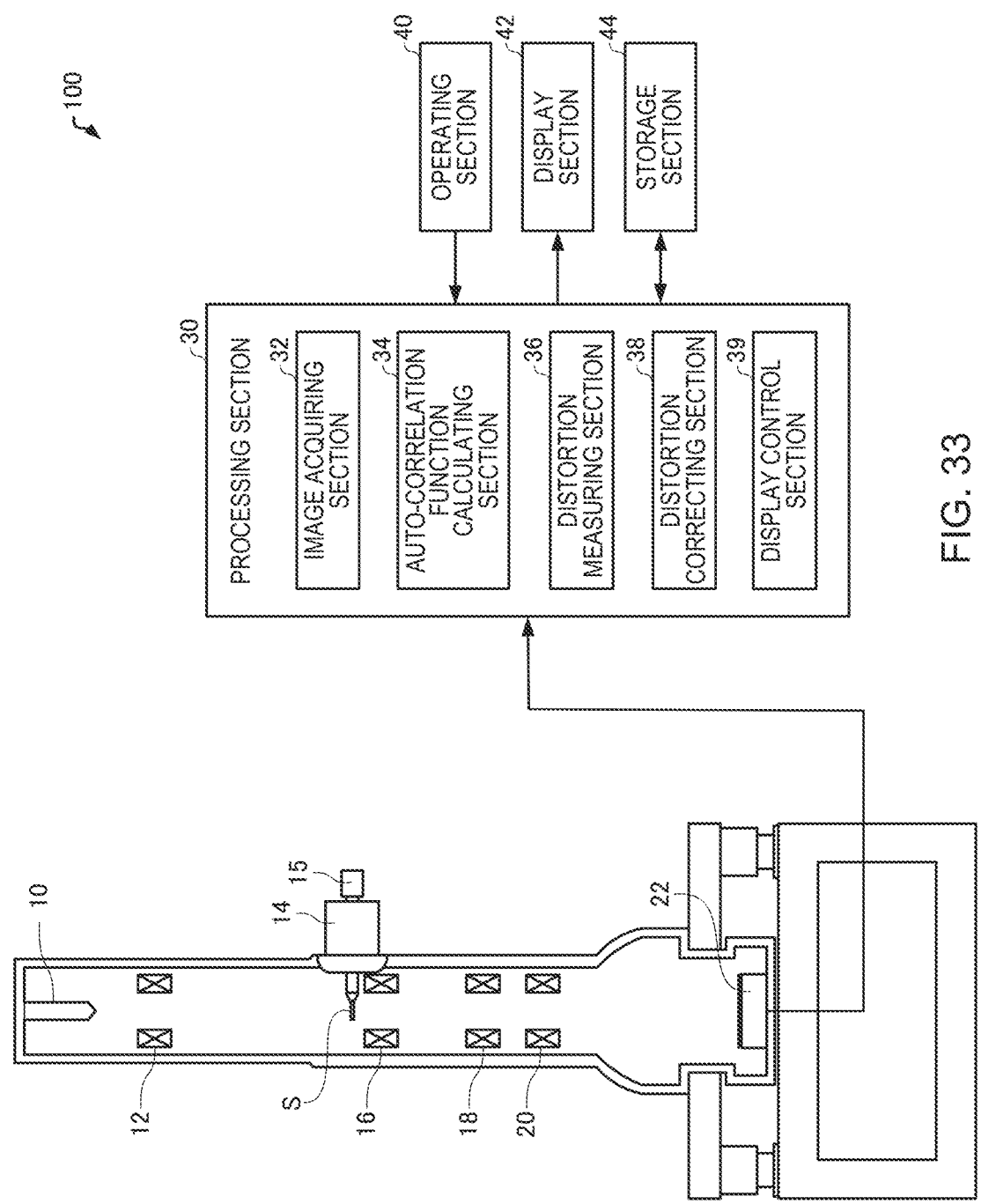
FIG. 33 is a diagram illustrating a configuration of an electron microscope according to the first embodiment.

Next, an electron microscope according to the first embodiment will be described with reference to the drawings. FIG. 33 is a diagram illustrating a configuration of an electron microscope 100 according to the first embodiment.

The electron microscope 100 is a transmission electron microscope (TEM). In other words, in the electron microscope 100, a transmission electron microscope image (a TEM image) can be acquired by illuminating a specimen S with an electron beam and imaging the electron beam transmitted through the specimen S. In addition, with the electron microscope 100, a TEM image of the distortion measurement specimen 1 is acquired and a distortion of the TEM image is measured using the distortion measurement method for an electron microscope image according to the first embodiment described above.

As illustrated in FIG. 33, the electron microscope 100 includes an electron source 10, an illumination lens 12, a specimen stage 14, a specimen holder 15, an objective lens 16, an intermediate lens 18, a projector lens 20, an imaging device 22, a processing section 30, an operating section 40, a display section 42, and a storage section 44.

The electron source 10 generates electrons. The electron source 10 is, for example, an electron gun which accelerates electrons emitted from a cathode by an anode and which emits an electron beam.

The illumination lens 12 causes the electron beam discharged from the electron source 10 to converge and illuminates a specimen S with the converged electron beam. Although not illustrated, the illumination lens 12 may be constituted by a plurality of electron lenses (condenser lenses).

The specimen stage 14 holds the specimen S. In the illustrated example, the specimen stage 14 holds the specimen S via the specimen holder 15. The specimen S can be positioned with the specimen stage 14. When measuring a distortion of a TEM image in the electron microscope 100, the distortion measurement specimen 1 is set on the specimen stage 14 (the specimen holder 15). Accordingly, the distortion measurement specimen 1 can be arranged on a specimen plane. Alternatively, the distortion measurement specimen 1 can be arranged on a plane conjugate to the specimen plane (the specimen stage 14) depending on an electron lens to be measured.

The objective lens 16 is a first-stage lens for forming a TEM image with an electron beam transmitted through the specimen S.

The intermediate lens 18 and the projector lens 20 enlarges the image formed by the objective lens 16 and produces an image on the imaging device 22. The objective lens 16, the intermediate lens 18, and the projector lens 20 constitute an imaging system of the electron microscope 100.

The imaging device 22 photographs an image formed by the imaging system. For example, the imaging device 22 is a digital camera such as a charge coupled device (CCD) camera or a complementary MOS (CMOS) camera.

Although not illustrated, the electron microscope 100 may include a lens, an aperture, and the like in addition to the optical systems described above. In addition, although not illustrated, the electron microscope 100 may be equipped with an analyzer such as an energy dispersive X-ray spectrometer or a wavelength-dispersive X-ray spectrometer.

With the electron microscope 100, an electron beam discharged from the electron source 10 is focused by the illumination lens 12 and illuminates the specimen S. The electron beam illuminating the specimen S is transmitted through the specimen S and imaged by the objective lens 16. The TEM image formed by the objective lens 16 is further enlarged by the intermediate lens 18 and the projector lens 20 and photographed by the imaging device 22. The TEM image (image data) photographed by the imaging device 22 is sent to the processing section 30.

The operating section 40 performs a process of acquiring an operation signal that corresponds to an operation performed by a user and sending the operation signal to the processing section 30. For example, the operating section 40 is constituted by a button, a key, a touch panel display, or a microphone.

The display section 42 displays an image generated by the processing section 30, and functions thereof can be implemented by an LCD, a CRT, or the like.

The storage section 44 serves as a work area for the processing section 30, and functions thereof can be implemented by a RAM, a ROM, a hard disk, or the like. The storage section 44 stores programs, data, and the like that enable the processing section 30 to perform various control processes and calculation processes. In addition, the storage section 44 is also used to temporarily store results of calculations and the like performed by the processing section 30 in accordance with various programs.

The processing section 30 performs processes such as a process of acquiring a TEM image of a distortion measurement specimen and measuring a distortion of the TEM image and a process of displaying a result of a measurement of the distortion on the display section 42. Functions of the processing section 30 can be realized by having various processors (a CPU, DSP, or the like) execute programs. Alternatively, at least a part of the functions of the processing section 30 may be realized by a dedicated circuit such as an ASIC (a gate array or the like). The processing section 30 includes an image acquiring section 32, an auto-correlation function calculating section 34, a distortion measuring section 36, a distortion correcting section 38, and a display control section 39.

The image acquiring section 32 acquires a TEM image of the distortion measurement specimen 1. The image acquiring section 32 accepts data (image data) of a TEM image of the distortion measurement specimen 1 output from the imaging device 22, and acquires the TEM image of the distortion measurement specimen 1.

The auto-correlation function calculating section 34 calculates an auto-correlation function of the TEM image of the distortion measurement specimen 1 acquired by the image acquiring section 32. The auto-correlation function calculating section 34 calculates the auto-correlation function of the TEM image by the method described above in the step of calculating an auto-correlation function (S202).

The distortion measuring section 36 measures a distortion of the TEM image of the distortion measurement specimen 1. Specifically, the distortion measuring section 36 measures a distortion of the TEM image from a pattern formed by connecting peak positions of the auto-correlation function calculated by the auto-correlation function calculating section 34. The distortion measuring section 36 measures the distortion of the TEM image by the method described above in the step of measuring a distortion of an electron microscope image (S204).

The distortion correcting section 38 performs a process of correcting a distortion of a photographed TEM image of the specimen S based on a measurement result of a distortion of the TEM image as measured by the distortion measuring section 36.

The display control section 39 performs a process of displaying, on the display section 42, the measurement result of a distortion of the TEM image as measured by the distortion measuring section 36. In addition, the display control section 39 performs control for displaying, on the display section 42, the TEM image of which a distortion has been corrected by the distortion correcting section 38.

Figure 34:
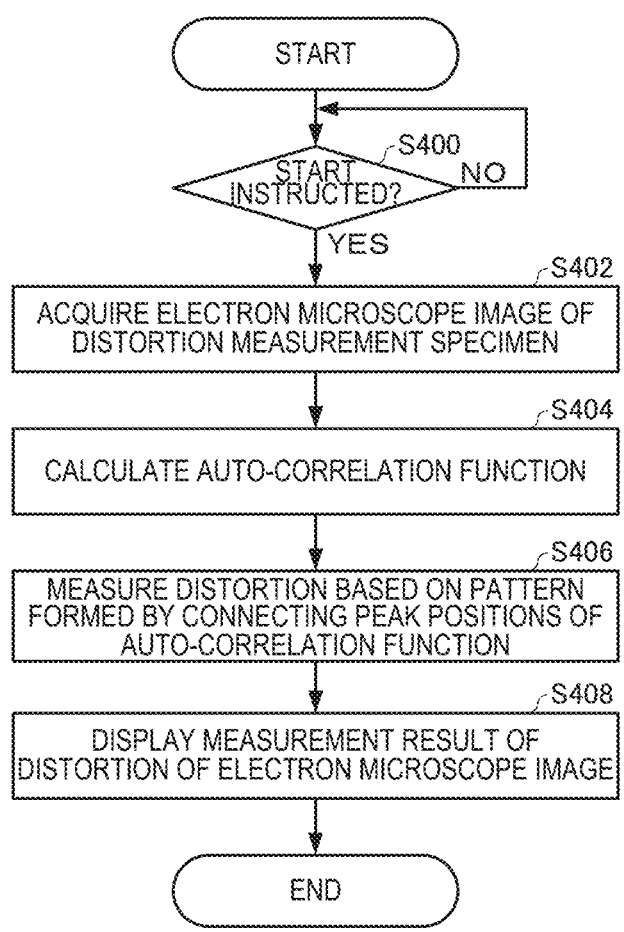
FIG. 34 is a flowchart illustrating an example of a flow of processes by a processing section of an electron microscope according to the first embodiment.

FIG. 34 is a flowchart illustrating an example of a flow of processes by the processing section 30 of the electron microscope 100 according to the first embodiment.

First, the distortion measurement specimen 1 is set on the specimen stage 14 (the specimen holder 15) and the distortion measurement specimen 1 is loaded to the electron microscope 100. An example in which the distortion measurement specimen 1 is loaded to a specimen plane and a distortion of an imaging system is measured will now be described.

The processing section 30 determines whether or not the user has issued an instruction to start distortion measurement (a measurement start instruction) (S400), and waits until a measurement start instruction is issued (NO in S400). For example, the processing section 30 determines that the user has issued a measurement start instruction when the measurement start instruction is input via the operating section 40.

When it is determined that a measurement start instruction has been issued (YES in S400), the image acquiring section 32 acquires a TEM image of the distortion measurement specimen 1 (S402). The image acquiring section 32 controls the optical systems 12, 16, 18, and 20 and the imaging device 22 to photograph the distortion measurement specimen 1 under observation conditions (magnification and the like) set in advance, accepts a TEM image from the imaging device 22, and acquires a TEM image of the distortion measurement specimen 1.

Next, the auto-correlation function calculating section 34 calculates an auto-correlation function of the acquired TEM image of the distortion measurement specimen 1 (S404).

Next, the distortion measuring section 36 measures a distortion of the TEM image based on a pattern formed by connecting peak positions of the calculated auto-correlation function (S406). A measurement result of the distortion of the TEM image is stored in the storage section 44.

Next, the display control section 39 performs control for displaying, on the display section 42, the measurement result of the distortion of the TEM image (S408). Subsequently, the processing section 30 ends the process.

With the electron microscope 100, when a TEM image of the specimen S is photographed after a distortion measurement of the TEM image is completed, the distortion correcting section 38 corrects the distortion of the TEM image of the specimen S based on the measurement result of the distortion of the TEM image stored in the storage section 44. Accordingly, with the electron microscope 100, a TEM image of the specimen S with no distortion (or reduced distortion) can be displayed on the display section 42.

For example, the electron microscope 100 has the following features.

With the electron microscope 100, the image acquiring section 32 acquires a TEM image of the distortion measurement specimen 1, the auto-correlation function calculating section 34 calculates an auto-correlation function of the TEM image of the distortion measurement specimen 1, and the distortion measuring section 36 measures a distortion of the TEM image based on a pattern formed by connecting peak positions of the auto-correlation function. Therefore, with the electron microscope 100, a distortion of a TEM image can be readily and accurately measured. In addition, with the electron microscope 100, a distortion of a TEM image can be automatically measured.

With the electron microscope 100, since the display control section 39 performs control for displaying, on the display section 42, a measurement result of a distortion of a TEM image as measured by the distortion measuring section 36, the user can be readily informed of a measurement result of a distortion.

With the electron microscope 100, the distortion correcting section 38 corrects a distortion of a photographed TEM image based on a measurement result of a distortion of the TEM image as measured by the distortion measuring section 36. Therefore, with the electron microscope 100, a TEM image with no distortion (or reduced distortion) can be provided.

4.2. Second Embodiment

Figure 35:
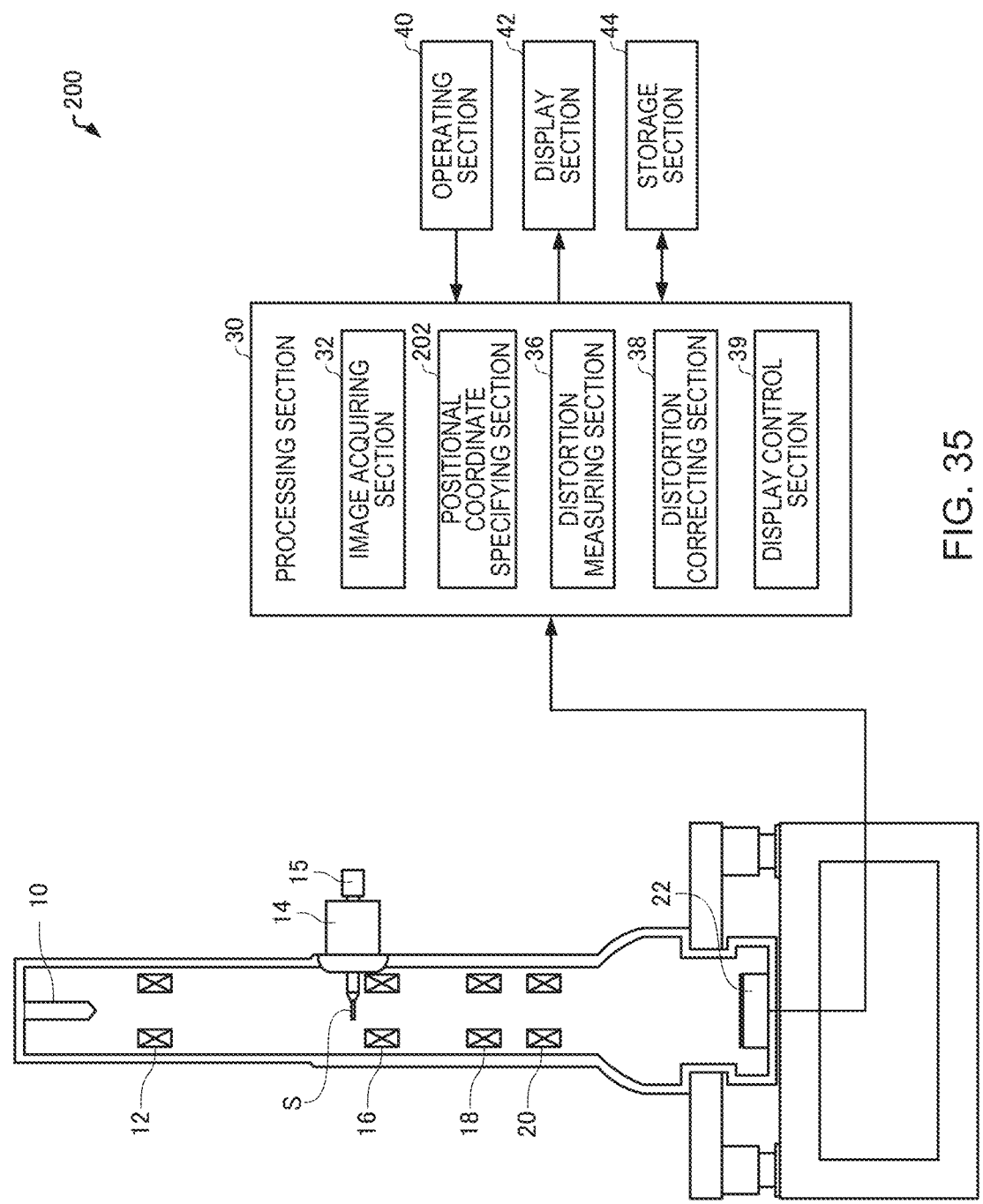
FIG. 35 is a diagram illustrating a configuration of an electron microscope according to the second embodiment.

Next, an electron microscope according to the second embodiment will be described with reference to the drawings. FIG. 35 is a diagram illustrating a configuration of an electron microscope 200 according to the second embodiment. Hereinafter, in the electron microscope 200 according to the second embodiment, members having similar functions to the components of the electron microscope 100 described above will be denoted by same reference characters and a detailed description thereof will be omitted.

The electron microscope 200 differs from the electron microscope 100 in that a TEM image of the distortion measurement specimen 1 is acquired and a distortion of the TEM image is measured using the distortion measurement method for an electron microscope image according to the second embodiment described above.

As illustrated in FIG. 35, the processing section 30 of the electron microscope 200 includes a positional coordinate specifying section 202.

The positional coordinate specifying section 202 calculates positional coordinates of the through-holes 9 on a TEM image of the distortion measurement specimen 1 acquired by the image acquiring section 32. The positional coordinate specifying section 202 calculates positional coordinates of the through-holes 9 by the method described above in the step of specifying positional coordinates of the through-holes 9 (S302).

The distortion measuring section 36 measures a distortion of a TEM image based on a pattern formed by connecting the specified positional coordinates of the through-holes 9. The distortion measuring section 36 measures the distortion of the TEM image by the method described above in the step of measuring a distortion of an electron microscope image (S304).

Figure 36:
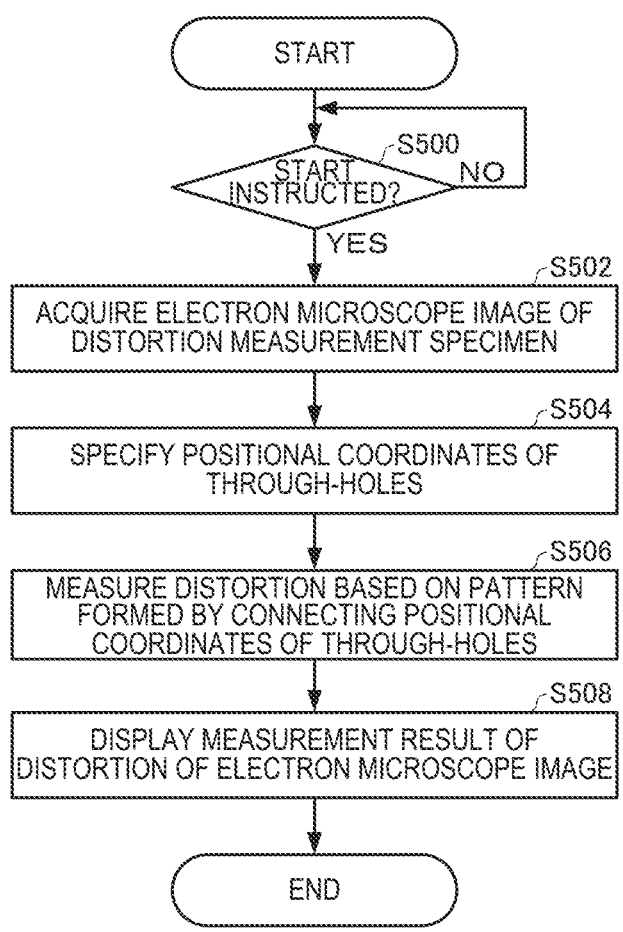
FIG. 36 is a flowchart illustrating an example of a flow of processes by a processing section of an electron microscope according to the second embodiment.

FIG. 36 is a flowchart illustrating an example of a flow of processes by the processing section 30 of the electron microscope 200 according to the second embodiment. The following description will focus on points that differ from the processes of the processing section 30 of the electron microscope 100 illustrated in FIG. 34 described above, and a description of similar points will be omitted.

First, the distortion measurement specimen 1 is set on the specimen stage 14 (the specimen holder 15) and the distortion measurement specimen 1 is loaded to the electron microscope 200.

The processing section 30 determines whether or not the user has issued an instruction to start distortion measurement (a measurement start instruction) (S500), and waits until a measurement start instruction is issued (NO in S500).

When it is determined that a measurement start instruction has been issued (YES in S500), the image acquiring section 32 acquires a TEM image of the distortion measurement specimen 1 (S502).

Next, the positional coordinate specifying section 202 specifies positional coordinates of the through-holes 9 on the acquired TEM image of the distortion measurement specimen 1 (S504).

The distortion measuring section 36 then measures a distortion of the TEM image based on a pattern formed by connecting the specified positional coordinates of the through-holes 9 (S506). A measurement result of the distortion of the TEM image is stored in the storage section 44.

Next, the display control section 39 performs control for displaying, on the display section 42, the measurement result of a distortion of the TEM image as measured by the distortion measuring section 36 (S508). In addition, the processing section 30 performs a process of storing the measurement result of the distortion of the TEM image in the storage section 44. Subsequently, the processing section 30 ends the process.

With the electron microscope 200, when a TEM image of the specimen S is photographed after a measurement of the distortion of the TEM image is completed, the distortion correcting section 38 corrects the distortion of the TEM image of the specimen S based on the measurement result of the distortion of the TEM image stored in the storage section 44.

For example, the electron microscope 200 has the following features.

With the electron microscope 200, the image acquiring section 32 acquires a TEM image of the distortion measurement specimen 1, the positional coordinate specifying section 202 specifies positional coordinates of the through-holes 9 on the TEM image of the distortion measurement specimen 1, and the distortion measuring section 36 measures a distortion of the TEM image based on a pattern formed by connecting the positional coordinates of the through-holes 9. Therefore, with the electron microscope 200, a distortion of a TEM image can be readily and accurately measured. In addition, with the electron microscope 200, a distortion of a TEM image can be automatically measured.

4.3. Third Embodiment

Figure 37:
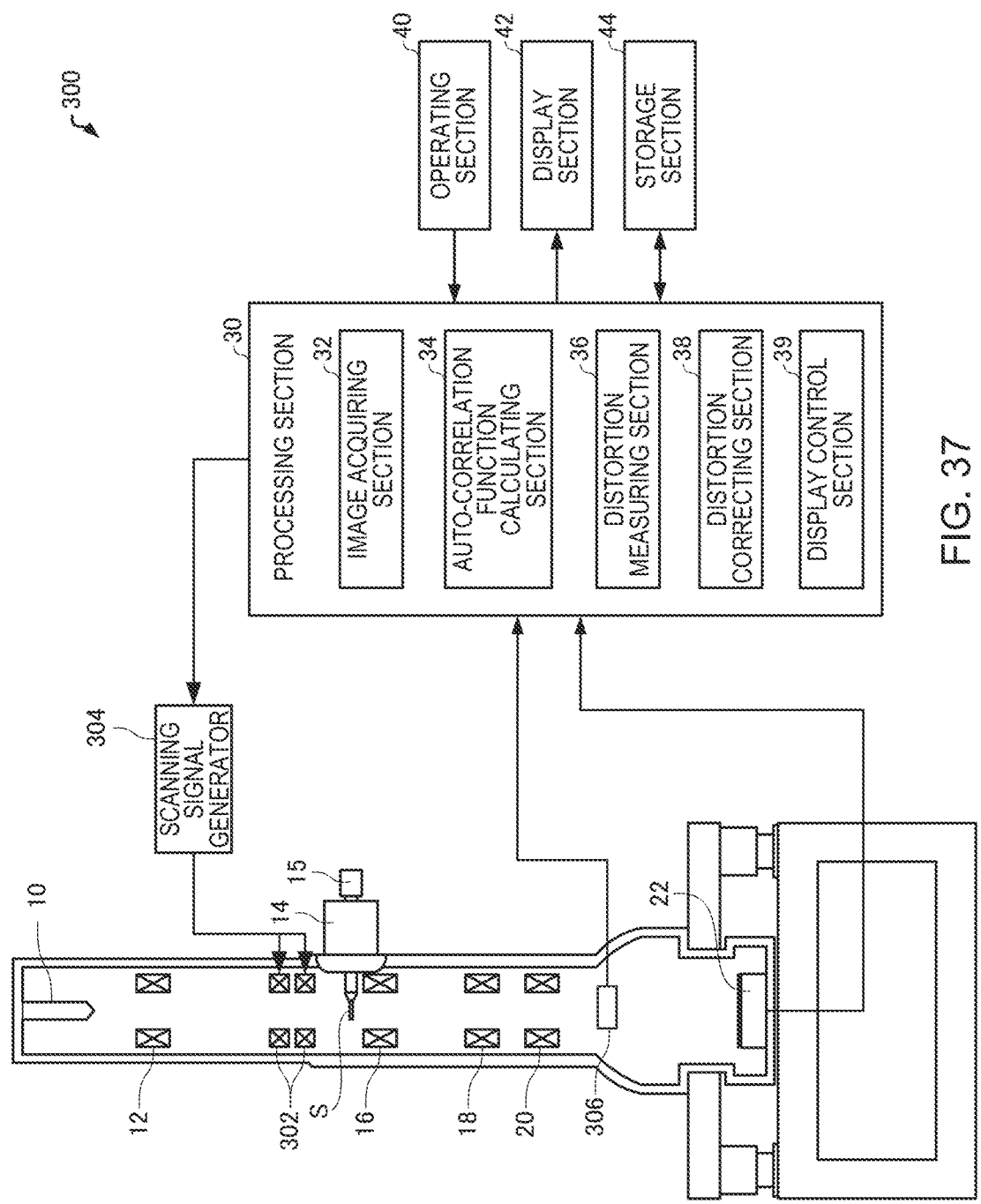
FIG. 37 is a diagram illustrating a configuration of an electron microscope according to the third embodiment.

Next, an electron microscope according to a third embodiment will be described with reference to the drawings. FIG. 37 is a diagram illustrating a configuration of an electron microscope 300 according to the third embodiment. Hereinafter, in the electron microscope 300 according to the third embodiment, members having similar functions to the components of the electron microscope 100 described above will be denoted by same reference characters and a detailed description thereof will be omitted.

The electron microscope 300 differs from the electron microscope 100 described above in that the electron microscope 300 is a scanning transmission electron microscope (STEM).

With the electron microscope 300, a scanning transmission electron microscope image (a STEM image) can be generated by scanning an electron probe (a focused electron beam) over the specimen S and acquiring intensity information of an electron beam transmitted through the specimen S for each illumination position of the electron beam. In addition, with the electron microscope 300, a STEM image of the distortion measurement specimen 1 is acquired and a distortion of the STEM image is measured using the distortion measurement method for an electron microscope image according to the first embodiment described above. It should be noted that the distortion measurement method for an electron microscope image according to the first embodiment can be applied to a STEM image in a similar manner to a TEM image.

As illustrated in FIG. 37, the electron microscope 300 includes a scanning deflector 302, a scanning signal generator 304 (a scanning signal generating section), and a STEM image detector 306.

The scanning deflector 302 causes an electron beam discharged from the electron source 10 to be deflected two-dimensionally. The scanning deflector 302 scans over the specimen S with an electron beam (an electron probe) focused by the illumination lens 12.

The scanning signal generator 304 generates a scanning signal to be supplied to the scanning deflector 302. Due to the scanning signal generator 304 supplying a scanning signal, the scanning deflector 302 can be operated based on the scanning signal and an electron probe can be scanned over the specimen S.

With a scanning electron microscope, a distortion of an obtained STEM image can be changed by varying scanning of the electron probe. For example, by varying a vertical to horizontal ratio of a region to be scanned with the electron probe, a vertical to horizontal ratio of an obtained STEM image can be changed. Therefore, with the electron microscope 300, the scanning signal generator 304 generates a scanning signal based on a measurement result of a distortion of the STEM image as measured by the processing section 30 (the distortion measuring section 36). As a result, with the electron microscope 300, a STEM image with no distortion (or reduced distortion) can be obtained.

Specifically, the processing section 30 sends information on a measurement result of a distortion stored in the storage section 44 to the scanning signal generator 304. In addition, based on the information on the measurement result of a distortion of an electron microscope image (a STEM image) from the processing section 30, the scanning signal generator 304 generates a scanning signal so that a STEM image with no distortion (or reduced distortion) is obtained.

The STEM image detector 306 detects an electron beam transmitted through the specimen S. For example, the STEM image detector 306 is a bright-field STEM detector which detects, among electrons having passed through the specimen S, electrons transmitted without being scattered as well as electrons scattered at angles equal to or smaller than a predetermined angle. The STEM image detector 306 sends an intensity signal (a detection signal) of a detected electron to a signal processing device (not illustrated). The signal processing device images the intensity signal (the detection signal) of the electron detected by the STEM image detector 306 in synchronization with the scanning signal, and generates a STEM image. The generated STEM image (image data) is sent to the processing section 30.

Alternatively, the STEM image detector 306 may be a dark-field STEM detector which detects electrons scattered at a specific angle by the specimen S. In addition, the electron microscope 300 may be equipped with both a bright-field STEM detector and a dark-field STEM detector.

Figure 38:
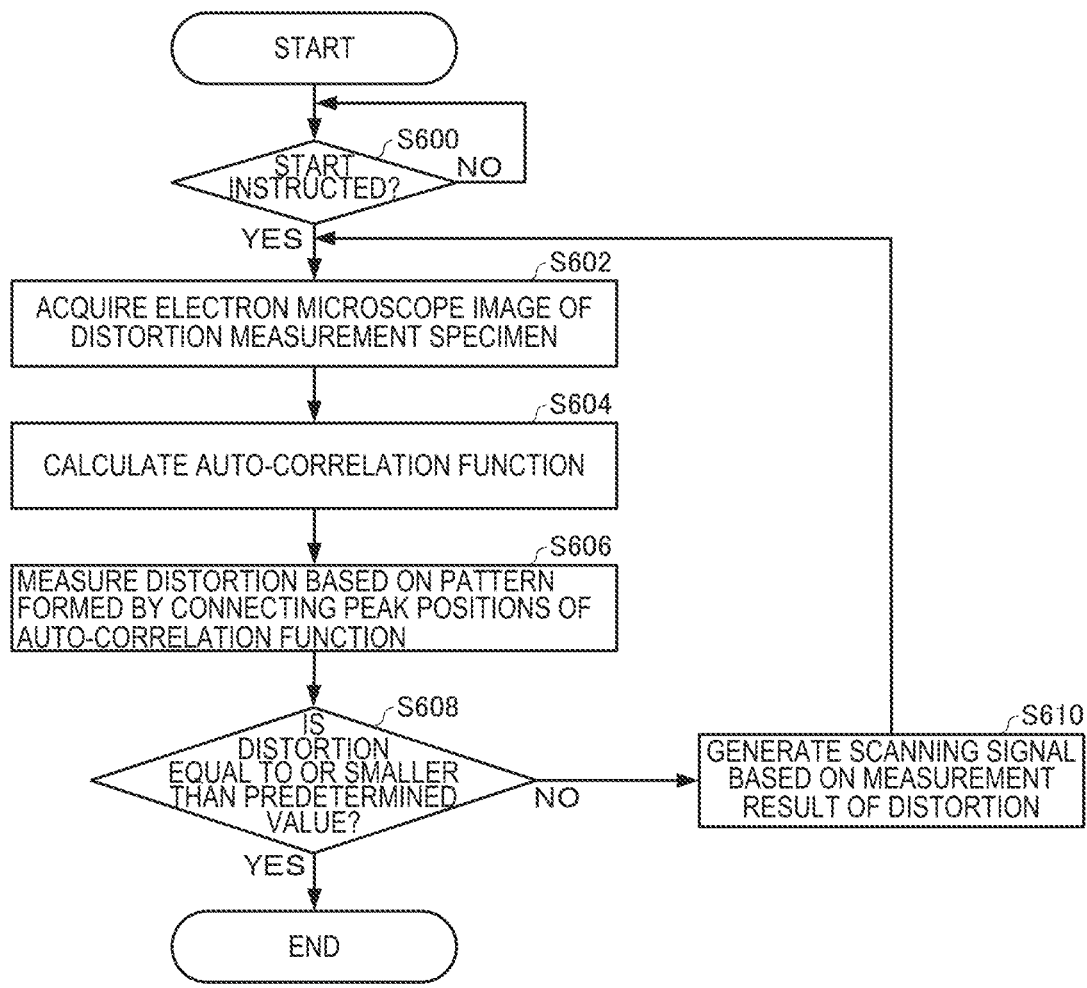
FIG. 38 is a flowchart illustrating an example of a flow of processes by a processing section of an electron microscope according to the third embodiment.

FIG. 38 is a flowchart illustrating an example of a flow of processes by the processing section 30 of the electron microscope 300 according to the third embodiment. The following description will focus on points that differ from the processes of the processing section 30 of the electron microscope 100 according to the third embodiment illustrated in FIG. 34 described above, and a description of similar points will be omitted.

First, the distortion measurement specimen 1 is set on the specimen stage 14 (the specimen holder 15) and the distortion measurement specimen 1 is loaded to the electron microscope 300.

The processing section 30 determines whether or not the user has issued an instruction to start distortion measurement (a measurement start instruction) (S600), and waits until a measurement start instruction is issued (NO in S600).

When it is determined that a measurement start instruction has been issued (YES in S600), the image acquiring section 32 acquires a STEM image of the distortion measurement specimen 1 (S602).

Next, the auto-correlation function calculating section 34 calculates an auto-correlation function of the acquired STEM image of the distortion measurement specimen 1 (S604).

Next, the distortion measuring section 36 measures a distortion of the STEM image based on a pattern formed by connecting peak positions of the calculated auto-correlation function (S606). A measurement result of the distortion of the STEM image is stored in the storage section 44.

Next, the distortion correcting section 38 performs a process of determining whether or not the measurement result of a distortion of the STEM image as measured by the distortion measuring section 36 is equal to or smaller than a predetermined value (S608). When the distortion correcting section 38 determines that the measured distortion of the STEM image is larger than the predetermined value (NO in S608), the distortion correcting section 38 sends the measurement result of the distortion of the STEM image stored in the storage section 44 to the scanning signal generator 304.

The scanning signal generator 304 accepts information on the measurement result of the distortion, and generates a scanning signal (corrects the scanning signal) based on the measurement result of the distortion (S610). Subsequently, a return is made to S602 and the image acquiring section 32 acquires a STEM image of the distortion measurement specimen 1, and the process of calculating an auto-correlation function (S604), the process of measuring a distortion (S606), and the process of determining whether or not the distortion is equal to or smaller than the predetermined value (S608) are performed.

When the distortion correcting section 38 determines that the measured distortion of the STEM image is equal to or smaller than the predetermined value (YES in S608), the processing section 30 ends the process. As a result, the STEM image of the specimen S obtained with the electron microscope 300 becomes an image with no distortion (or reduced distortion).

With the electron microscope 300, similar effects to those of the electron microscope 100 described above can be achieved. In addition, with the electron microscope 300, the scanning signal generator 304 generates a scanning signal based on a measurement result of a distortion of the STEM image as measured by the distortion measuring section 36. Therefore, with the electron microscope 300, a STEM image with no distortion (or reduced distortion) can be acquired.

4.4. Fourth Embodiment

Figure 39:
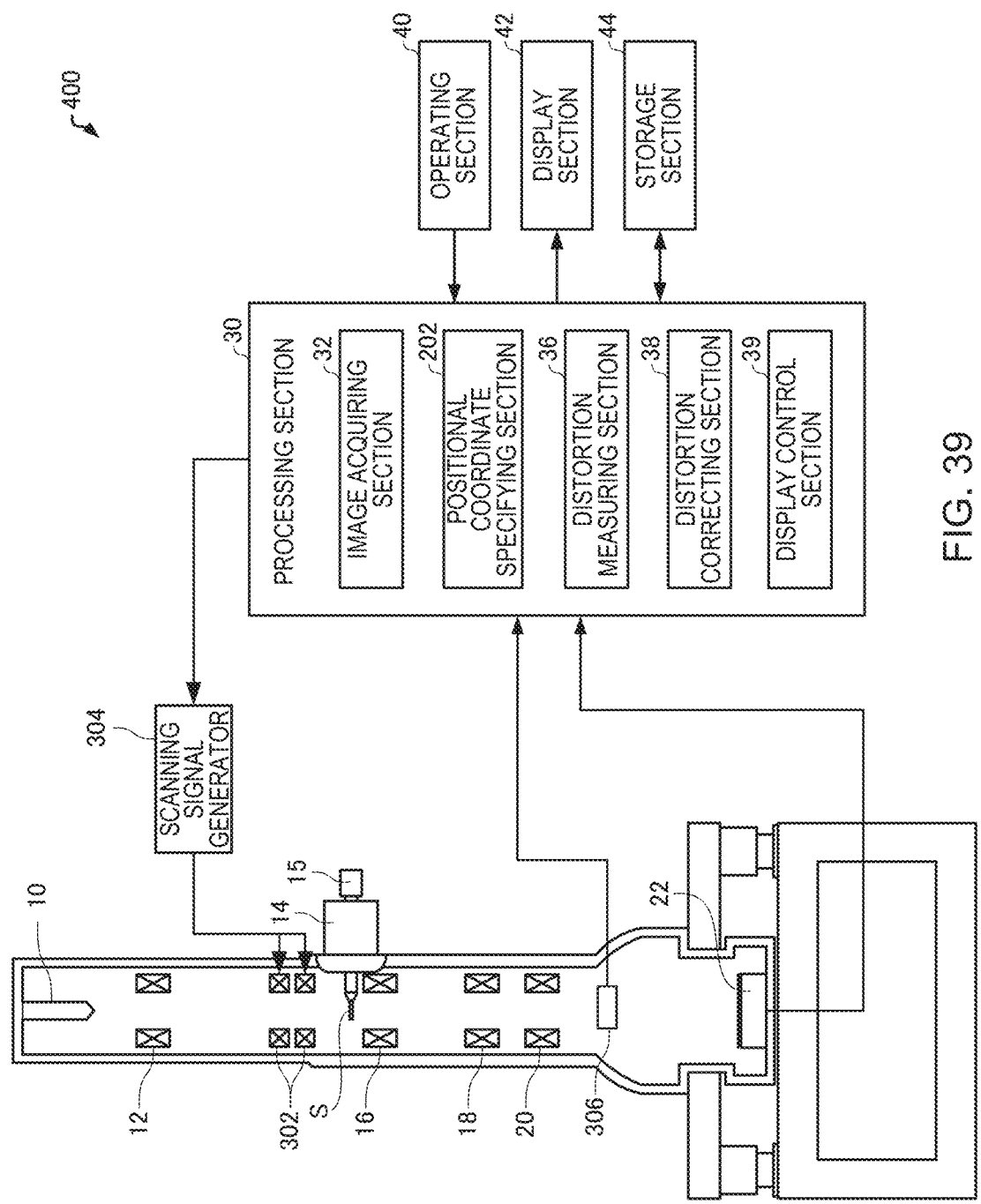
FIG. 39 is a diagram illustrating a configuration of an electron microscope according to the fourth embodiment.

Next, an electron microscope according to a fourth embodiment will be described with reference to the drawings. FIG. 39 is a diagram illustrating a configuration of an electron microscope 400 according to the fourth embodiment. Hereinafter, in the electron microscope 400 according to the fourth embodiment, members having similar functions to the components of the electron microscopes 100, 200, and 300 described above will be denoted by same reference characters and a detailed description thereof will be omitted.

The electron microscope 400 differs from the electron microscope 200 described above in that the electron microscope 400 is a scanning transmission electron microscope (STEM).

With the electron microscope 400, a STEM image of the distortion measurement specimen 1 is acquired and a distortion of the STEM image is measured using the distortion measurement method for an electron microscope image according to the second embodiment described above. It should be noted that the distortion measurement method for an electron microscope image according to the second embodiment can be applied to a STEM image in a similar manner to a TEM image.

As illustrated in FIG. 39, the electron microscope 400 includes the scanning deflector 302, the scanning signal generator 304, and the STEM image detector 306.

Figure 40:
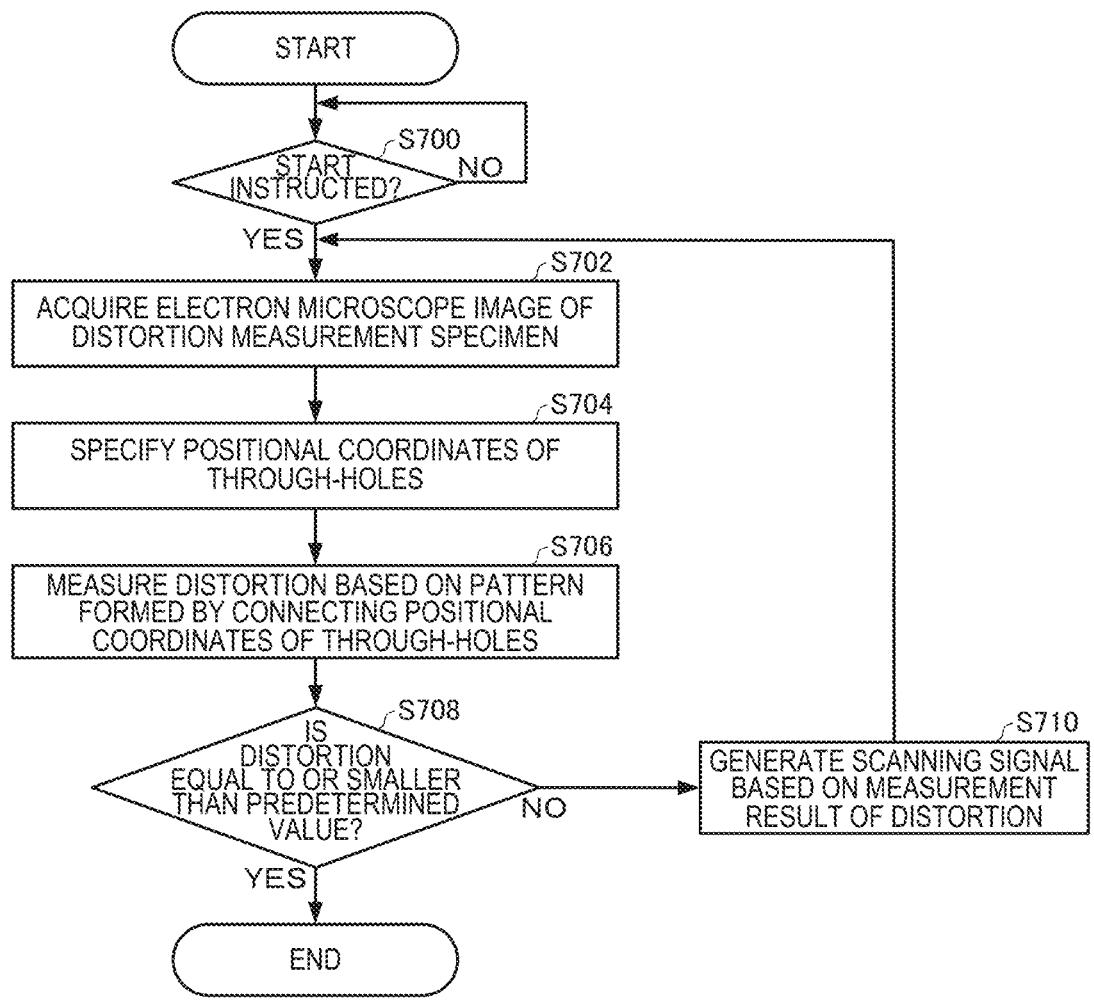
FIG. 40 is a flowchart illustrating an example of a flow of processes by a processing section of an electron microscope according to the fourth embodiment.

FIG. 40 is a flowchart illustrating an example of a flow of processes by the processing section 30 of the electron microscope 400 according to the fourth embodiment. The following description will focus on points that differ from the processes of the processing section 30 of the electron microscope 200 according to the second embodiment illustrated in FIG. 36 described above, and a description of similar points will be omitted.

First, the distortion measurement specimen 1 is set on the specimen stage 14 (the specimen holder 15) and the distortion measurement specimen 1 is loaded to the electron microscope 400.

The processing section 30 determines whether or not the user has issued an instruction to start distortion measurement (a measurement start instruction) (S700), and waits until a measurement start instruction is issued (NO in S700).

When it is determined that a measurement start instruction has been issued (YES in S700), the image acquiring section 32 acquires a STEM image of the distortion measurement specimen 1 (S702).

Next, the positional coordinate specifying section 202 specifies positional coordinates of the through-holes 9 on the acquired STEM image of the distortion measurement specimen 1 (S704).

The distortion measuring section 36 then measures a distortion of the STEM image based on a pattern formed by connecting the specified positional coordinates of the through-holes 9 (S706). A measurement result of the distortion of the STEM image is stored in the storage section 44.

Next, the distortion correcting section 38 performs a process of determining whether or not the measurement result of the distortion of the STEM image as measured by the distortion measuring section 36 is equal to or smaller than a predetermined value (S708). When the distortion correcting section 38 determines that the measured distortion of the STEM image is larger than the predetermined value (NO in S708), the distortion correcting section 38 sends the measurement result of the distortion of the STEM image stored in the storage section 44 to the scanning signal generator 304.

The scanning signal generator 304 accepts information on the measurement result of the distortion, and generates a scanning signal based on the measurement result of the distortion (S710). Subsequently, a return is made to S702 and the image acquiring section 32 acquires a STEM image of the distortion measurement specimen 1, and the process of specifying positional coordinates of the through-holes 9 (S704), the process of measuring a distortion (S706), and the process of determining whether or not the distortion is equal to or smaller than the predetermined value (S708) are performed.

When the distortion correcting section 38 determines that the measured distortion of the STEM image is equal to or smaller than the predetermined value (YES in S708), the processing section 30 ends the process. As a result, the STEM image of the specimen S obtained with the electron microscope 400 becomes an image with no distortion (or reduced distortion).

With the electron microscope 400, similar effects to those of the electron microscope 200 described above can be achieved. In addition, with the electron microscope 400, the scanning signal generator 304 generates a scanning signal based on a measurement result of the distortion of the STEM image as measured by the distortion measuring section 36. Therefore, with the electron microscope 400, a STEM image with no distortion (or reduced distortion) can be acquired.

5. Modifications

The invention is not limited to the embodiments described above, and various modifications and variations of the above embodiments may be made without departing from the scope of the invention.

Figure 41:
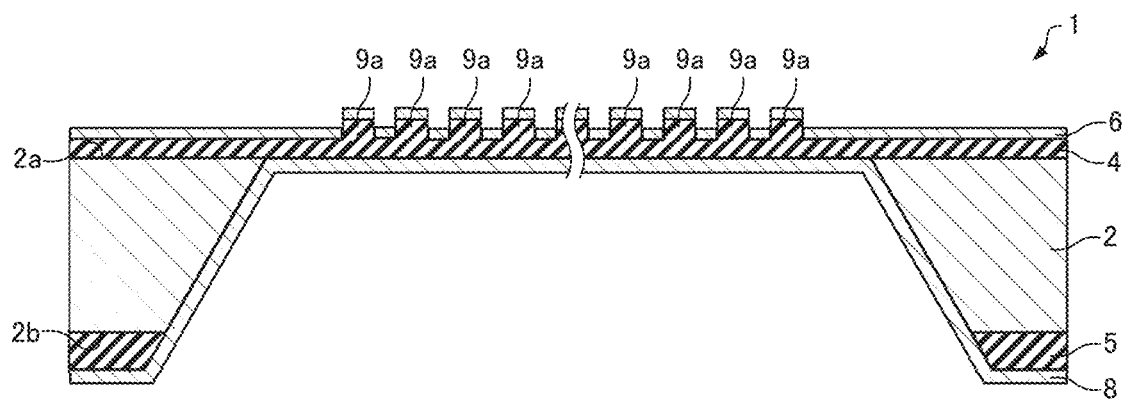
FIG. 41 is a sectional view schematically illustrating a modification of a distortion measurement specimen.
Figure 42:
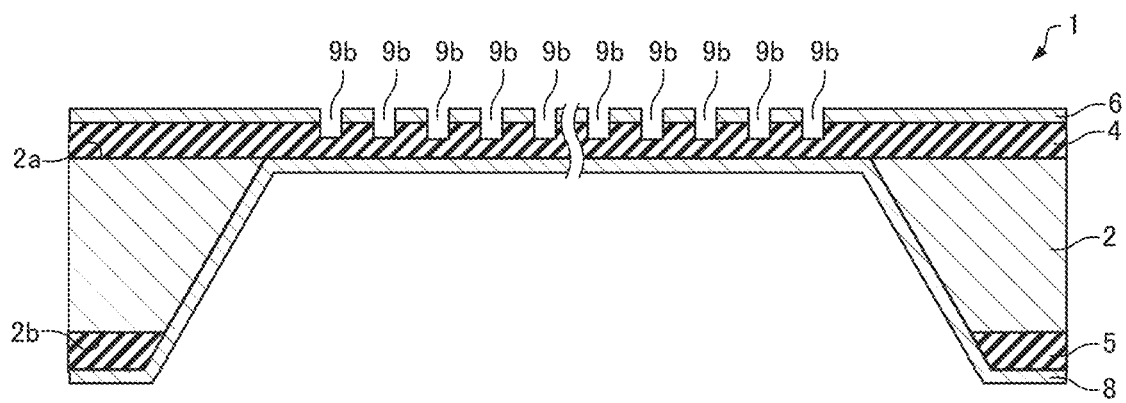
FIG. 42 is a sectional view schematically illustrating a modification of a distortion measurement specimen.

For example, although the distortion measurement specimen 1 has the pattern-formed layer 4 in which through-holes 9 arranged in a lattice are formed as illustrated in FIGS. 1 and 2 in the embodiments described above, structures arranged in a lattice on the pattern-formed layer 4 are not limited to the through-holes 9. The structures formed on the pattern-formed layer 4 need only enable a lattice pattern to be confirmed on an electron microscope image (a TEM image or a STEM image) obtained by photographing the distortion measurement specimen 1. For example, the structures formed on the pattern-formed layer 4 may be projected portions 9a formed on the pattern-formed layer 4 as illustrated in FIG. 41 or bottomed holes or, in other words, recessed portions 9b as illustrated in FIG. 42. In addition, the structures may be made of a different material from the pattern-formed layer 4. The projected portions 9a and the recessed portions 9b can be formed using a semiconductor manufacturing technique in a similar manner to the through-holes 9.

Furthermore, for example, although the electron microscope 300 described above is a scanning transmission electron microscope (STEM), the electron microscope 300 may instead be a scanning electron microscope (SEM). Even in this case, a distortion of a SEM image can be measured and a SEM image with no distortion (or reduced distortion) can be obtained in a similar manner. The same applies to the electron microscope 400 described above.

It should be noted that the embodiments and the modifications described above are merely examples and the invention is not limited thereto. For example, the respective embodiments and the respective modifications may be combined as appropriate.

The invention includes various other configurations which are substantially the same as the configurations described in the embodiments (for example, configurations having the same functions, methods, and results or configurations having the same objectives and effects). In addition, the invention includes various other configurations obtained by replacing nonessential portions of the configurations described in the embodiments. Furthermore, the invention includes various other configurations capable of producing the same effects or configurations capable of achieving the same objectives as the configurations described in the embodiments. Moreover, the invention includes various other configurations obtained by adding known art to the configurations described in the embodiments.

While some embodiments of the invention have been described in detail above, a person skilled in the art will readily appreciate that various modifications can be made without materially departing from the novel teachings and effects of the invention. Accordingly, all such modifications are assumed to be included in the scope of the invention.

What is claimed is:

1. A distortion measurement method for an electron microscope image, the method comprising:
    loading a distortion measurement specimen having structures arranged in a lattice to a specimen plane of an electron microscope or a plane conjugate to the specimen plane to obtain an electron microscope image of the distortion measurement specimen; and
    measuring a distortion from the obtained electron microscope image of the distortion measurement specimen, wherein the distortion comprises changes in an aspect ratio of the obtained electron microscope image;
    wherein the step of measuring the distortion comprises:
        calculating an auto-correlation function of the electron microscope image of the distortion measurement specimen; and
        measuring the distortion based on a pattern formed by connecting peak positions of the auto-correlation function, wherein the pattern is an ellipse.

2. The distortion measurement method according to claim 1, wherein the ellipse is a concentric ellipse.

3. The distortion measurement method according to claim 1,
    wherein the distortion measurement specimen comprises:
    a substrate; and
    a pattern-formed layer supported by the substrate and including the structures,
    wherein the structures are at least one of through-holes, projected portions, and recessed portions.

4. An electron microscope configured to measure a distortion of an electron microscope image, the electron microscope comprising:
    an image acquiring section that acquires an electron microscope image of a distortion measurement specimen having structures arranged in a lattice;
    a distortion measuring section that measures a distortion from the electron microscope image of the distortion measurement specimen, wherein the distortion comprises changes in an aspect ratio of the obtained electron microscope image; and
    an auto-correlation function calculating section that calculates an auto-correlation function of the electron microscope image of the distortion measurement specimen;
    wherein the distortion measuring section measures the distortion based on a pattern formed by connecting peak positions of the auto-correlation function, wherein the pattern is an ellipse.

5. The electron microscope according to claim 4, further comprising:
    a display control section that performs control to cause a measurement result of the distortion as measured by the distortion measuring section to be displayed on a display section.

6. The electron microscope according to claim 4, further comprising:
    a distortion correcting section that corrects a distortion of a photographed electron microscope image based on a measurement result of the distortion as measured by the distortion measuring section.

7. The electron microscope according to claim 4, further comprising:
    a scanning signal generating section that generates a scanning signal based on a measurement result of the distortion as measured by the distortion measuring section; and
    a scanning deflector that scans over a specimen with an electron beam in response to the scanning signal.

8. A distortion measurement specimen for measuring a distortion of an electron microscope image, the distortion measurement specimen comprising:
    a substrate;
    a pattern-formed layer supported by the substrate and including through-holes arranged in a lattice, wherein the pattern-formed layer is formed on a first surface of the substrate;
    a first conductive layer; and
    a second conductive layer;
    wherein a portion of the pattern-formed layer is sandwiched between the first conductive layer and the second conductive layer, wherein the portion includes the through-holes and the through-holes penetrate the first conductive layer, the pattern-formed layer, and the second conductive layer.

9. A method of manufacturing a distortion measurement specimen for measuring a distortion of an electron microscope image, the method comprising:
    preparing a substrate;
    forming a first layer on a first surface of the substrate;
    forming structures arranged in a lattice by patterning the first layer;
    etching a second surface on an opposite side to the first surface of the substrate to remove the substrate;
    forming a first conductive layer on an upper surface of the first layer, wherein the first conductive layer comprises a conductive material; and
    forming a second conductive layer on a lower surface of the first layer, wherein the first conductive layer comprises a conductive material.

10. The method of manufacturing the distortion measurement specimen according to claim 9,
    wherein, in the step of forming structures, a resist for patterning the first layer is exposed by an electron-beam lithography system.

11. The method of manufacturing the distortion measurement specimen according to claim 10,
    wherein, in the step of forming structures, etching of the first layer is performed by using an inductively-coupled plasma etching device.

12. The method of manufacturing the distortion measurement specimen according to claim 9,
    wherein, in the step of forming the first layer, the first layer is formed so that the first layer is imparted with tensile stress.

13. The method of manufacturing a distortion measurement specimen according to claim 9,
    wherein the structures are at least one of through-holes, projected portions, and recessed portions, and
    wherein a shape of the structures as viewed from a thickness direction of the first layer is a circle.

14. A distortion measurement method for an electron microscope image, the method comprising:
  measuring a distortion of an electron microscope image by using an electron microscope image of a distortion measurement specimen, wherein the distortion measurement specimen comprises:
    a substrate, and
    a pattern-formed layer supported by the substrate and including structures arranged in a lattice;
  calculating an auto-correlation function of the electron microscope image of the distortion measurement specimen; and
  measuring the distortion based on a pattern formed by connecting peak positions of the auto-correlation function, wherein the pattern is an ellipse.

* * * * *